US008841259B2

(12) United States Patent
Feener et al.

(10) Patent No.: US 8,841,259 B2
(45) Date of Patent: Sep. 23, 2014

(54) COMPOSITIONS AND METHODS FOR TREATING VASCULAR PERMEABILITY

(75) Inventors: Edward P. Feener, North Reading, MA (US); Lloyd P. Aiello, Belmont, MA (US)

(73) Assignee: Joslin Diabetes Center, Boston, MA (US)

( * ) Notice: Subject to any disclaimer, the term of this patent is extended or adjusted under 35 U.S.C. 154(b) by 928 days.

(21) Appl. No.: 11/884,503

(22) PCT Filed: Feb. 16, 2006

(86) PCT No.: PCT/US2006/005395
§ 371 (c)(1), (2), (4) Date: Mar. 27, 2008

(87) PCT Pub. No.: WO2006/091459
PCT Pub. Date: Aug. 31, 2006

(65) Prior Publication Data
US 2008/0280811 A1 Nov. 13, 2008

Related U.S. Application Data

(60) Provisional application No. 60/656,167, filed on Feb. 24, 2005, provisional application No. 60/725,820, filed on Oct. 12, 2005.

(51) Int. Cl.
A61K 38/00 (2006.01)
C12Q 1/68 (2006.01)
G01N 33/68 (2006.01)
C12Q 1/527 (2006.01)
A61K 38/17 (2006.01)

(52) U.S. Cl.
CPC .......... *A61K 38/1709* (2013.01); *C12Q 1/6883* (2013.01); *G01N 2800/32* (2013.01); *C12Q 2600/136* (2013.01); *G01N 33/6893* (2013.01); *C12Q 1/527* (2013.01); *C12Q 2600/158* (2013.01)
USPC ....................................................... 514/20.8

(58) Field of Classification Search
None
See application file for complete search history.

(56) References Cited

U.S. PATENT DOCUMENTS

| | | |
|---|---|---|
| 3,832,253 A | 8/1974 | Di Palma et al. |
| 3,854,480 A | 12/1974 | Zaffaroni |
| 4,452,775 A | 6/1984 | Kent |
| 4,522,811 A | 6/1985 | Eppstein et al. |
| 4,667,014 A | 5/1987 | Nestor, Jr. et al. |
| 4,748,034 A | 5/1988 | de Rham |
| 4,987,071 A | 1/1991 | Cech et al. |
| 5,075,109 A | 12/1991 | Tice et al. |
| 5,093,246 A | 3/1992 | Cech et al. |
| 5,116,742 A | 5/1992 | Cech et al. |
| 5,239,660 A | 8/1993 | Ooi |
| 5,652,122 A | 7/1997 | Frankel et al. |
| 5,663,143 A | 9/1997 | Ley et al. |
| 5,670,617 A | 9/1997 | Frankel et al. |
| 5,747,641 A | 5/1998 | Frankel et al. |
| 5,773,442 A | 6/1998 | Akamatsu et al. |
| 5,780,265 A | 7/1998 | Dennis et al. |
| 5,786,328 A * | 7/1998 | Dennis et al. ............ 514/12 |
| 5,795,865 A * | 8/1998 | Markland et al. ............ 514/12 |
| 5,804,604 A | 9/1998 | Frankel et al. |
| 5,837,500 A | 11/1998 | Ladner et al. |
| 5,861,484 A | 1/1999 | Kendall et al. |
| 5,994,125 A | 11/1999 | Markland et al. |
| 6,010,880 A | 1/2000 | Markland et al. |
| 6,057,287 A | 5/2000 | Markland et al. |
| 6,071,723 A | 6/2000 | Markland et al. |
| 6,103,499 A | 8/2000 | Markland et al. |
| 6,156,785 A | 12/2000 | Stefansson et al. |
| 6,168,587 B1 | 1/2001 | Bellhouse et al. |
| 6,194,389 B1 | 2/2001 | Johnston et al. |
| 6,331,313 B1 | 12/2001 | Wong et al. |
| 6,333,402 B1 | 12/2001 | Markland et al. |
| 6,423,498 B1 | 7/2002 | Markland et al. |
| 6,468,798 B1 | 10/2002 | Debs et al. |
| 6,471,996 B1 | 10/2002 | Sokoll et al. |
| 6,472,375 B1 | 10/2002 | Hoon et al. |
| 6,503,713 B1 | 1/2003 | Rana |
| 6,579,895 B2 | 6/2003 | Karim et al. |
| 7,625,944 B2 | 12/2009 | Sinha et al. |
| 2001/0034023 A1 | 10/2001 | Stanton, Jr. et al. |
| 2002/0055458 A1* | 5/2002 | Stefansson ............ 514/1 |
| 2003/0069258 A1 | 4/2003 | Lam et al. |
| 2003/0180285 A1 | 9/2003 | Burnie |
| 2004/0171794 A1 | 9/2004 | Ladner et al. |
| 2004/0209797 A1 | 10/2004 | Karas |
| 2004/0209863 A1 | 10/2004 | Pinto et al. |
| 2005/0130897 A1 | 6/2005 | Ma |
| 2005/0223416 A1 | 10/2005 | Nuijens et al. |

(Continued)

FOREIGN PATENT DOCUMENTS

| | | |
|---|---|---|
| WO | WO 02/13800 | 2/2002 |
| WO | WO 2004/032911 | 4/2004 |

(Continued)

OTHER PUBLICATIONS

Gao et al. Diabetologia, 2003, 46:689-698.*
Han Lee et al. "Approaches toward reversal of increased vascular permeability in C1 inhibitor deficient mice", Immun. Letts, 2003, 89:155-160.*
Brenda Information for Plasma Kallikrein EC 3.4.21.34 < http://www.brenda-enzymes.org/php/flat_result.php4?ecno=3.4.21.34 &organism_list=&Suchword=&UniProtAcc=#ORGANISM > visited Sep. 17, 2013.*

(Continued)

*Primary Examiner* — Suzanne M Noakes
(74) *Attorney, Agent, or Firm* — McNeill Baur PLLC

(57) ABSTRACT

The present invention provides methods and composition for the treatment and diagnosis of disorders associated with excessive vascular permeability and edema.

19 Claims, 8 Drawing Sheets

(56) References Cited

U.S. PATENT DOCUMENTS

| | | | |
|---|---|---|---|
| 2006/0018896 | A1 | 1/2006 | Schwaeble et al. |
| 2006/0189534 | A1 | 8/2006 | Ma |
| 2007/0270344 | A1 | 11/2007 | Belichard |
| 2008/0038276 | A1 | 2/2008 | Sinha et al. |
| 2008/0280811 | A1 | 11/2008 | Feener et al. |
| 2009/0069231 | A1 | 3/2009 | Aiello et al. |
| 2010/0273721 | A1 | 10/2010 | Belichard |

FOREIGN PATENT DOCUMENTS

| | | |
|---|---|---|
| WO | WO 2005/041887 | 5/2005 |
| WO | WO 2005/099691 | 10/2005 |
| WO | WO 2006/091459 | 8/2006 |
| WO | WO 2007/044932 | 4/2007 |
| WO | WO 2008/016883 | 2/2008 |
| WO | WO 2008/091692 | 7/2008 |
| WO | WO 2009/097141 | 8/2009 |

OTHER PUBLICATIONS

Abbate et al., "Carbonic Anhydrase Inhibitors: E7070, A Sulfonamide Anticancer Agent, Potently Inhibits Cytosolic Isozymes I and II, and Transmembrane, Tumor-Associated Isozyme IX," *Bioorg. Med. Chem. Lett.* 14:217-223, 2004.

Abdouh et al., "Early Upregulation of Kinin B1 Receptors in Retinal Microvessels of the Streptozotocin-Diabetic Rat," *Br. J. Pharmacol.* 140:33-40, 2003.

Aiello et al., "Vascular Endothelial Growth Factor in Ocular Fluid of Patients with Diabetic Retinopathy and Other Retinal Disorders," *N. Engl. J. Med.* 331:1480-1487, 1994.

Akita et al., "Protective Effect of C1 Esterase Inhibitor on Reperfusion Injury in the Rat Middle Cerebral Artery Occlusion Model," *Neurosurgery* 52:395-400, 2003.

Almdal et al., "The Independent Effect of Type 2 Diabetes Mellitus on Ischemic Heart Disease, Stroke, and Death: A Population-Based Study of 13,000 Men and Women with 20 Years of Follow-Up," *Arch. Intern. Med.* 164-1422-1426, 2004.

Arevalo et al., "Primary Intravitreal Bevacizumab (Avastin) for Diabetic Macular Edema: Results from the Pan-American Collaborative Retina Study Group at 6-month Follow-up," *Ophthalmology* 114:743-750, 2007.

Bagella et al., "Cloning of Murine CDK9/PITALRE and Its Tissue-Specific Expression in Development," *J. Cell. Physiol.* 177:206-213, 1998.

Barber et al., "The Ins2Akita Mouse as a Model of Early Retinal Complications in Diabetes," *Invest. Ophthalmol Vis. Sci.* 46:2210-2218, 2005.

Bhoola et al., "Bioregulation of Kinins: Kallikreins, Kininogens, and Kininases," *Pharm. Rev.* 44:1-80, 1992.

Blasko et al., "How Chronic Inflammation Can Affect the Brain and Support the Development of Alzheimer's Disease in Old Age: The Role of Microglia and Astrocytes," *Aging Cell* 3:169-176, 2004.

Bloechle et al., "Inhibition of Bradykinin $B_2$ Receptor Preserves Microcirculation in Experimental Pancreatitis in Rats," *Am. J. Physiol.* 247:G42-G51, 1998.

Bork et al., "Treatment of Acute Edema Attacks in Hereditary Angioedema with a Bradykinin Receptor-2 Antagonist (Icatibant)," *J. Allergy. Clin. Immunol.* 119:1497-1503, 2007.

Bos et al., "The Functional Integrity of the Serpin Domain of C1-Inhibitor Depends on the Unique N-Terminal Domain, as Revealed by a Pathological Mutant," *J. Biol. Chem.* 278:29463-29470, 2003.

Bouchie et al., "Natriuretic Factors and Nitric Oxide Suppress Plasminogen Activator Inhibitor-1 Expression in Vascular Smooth Muscle Cells. Role of cGMP in the Regulation of the Plasminogen System," *Arterioscler. Thromb. Vasc. Biol.* 18:1771-1779, 1998.

Bouchie et al., "P2Y Receptor Regulation of PAI-1 Expression in Vascular Smooth Muscle Cells," *Arterioscler. Thromb. Vasc. Biol.* 20:866-873, 2000.

Brenner et al., "Effects of Losartan on Renal and Cardiovascular Outcomes in Patients with Type 2 Diabetes and Nephropathy," *N. Engl. J. Med.* 345:851-860, 2001.

Brott et al., "Early Hemorrhage Growth in Patients with Intracerebral Hemorrhage," *Stroke* 28:1-5, 1997.

Caliezi et al., "C1-Esterase Inhibitor: An Anti-Inflammatory Agent and Its Potential Use in the Treatment of Diseases Other Than Hereditary Angioedema," *Pharmacol. Rev.* 52:91-112, 2000.

Campbell et al., "Towards Understanding the Kallikrein-Kinin System: Insights from Measurement of Kinin Peptides," *Braz. J. Med. Biol. Res.* 33:665-677, 2000.

Campbell, "The Kallikrein-Kinin System in Humans," *Clin. Exp. Pharmacol. Physiol.* 28:1060-1065, 2001.

Carugati et al., "C1-Inhibitor Deficiency and Angioedema," *Mol. Immunol.* 38:161-173, 2001.

Casini et al., "Carbonic Anhydrase Inhibitors: Topically Acting Antiglaucoma Sulfonamides Incorporating Esters and Amides of 3- and 4-Carboxybenzolamide," *Bioorg. Med. Chem. Lett.* 13:2867-73, 2003.

Cecchi et al., "Carbonic Anhydrase Inhibitors: Synthesis and Inhibition of Cytosolic/Tumor-Associated Carbonic Anhydrase Isozymes I, II, and IX with Sulfonamides Derived from 4-Isothiocyanato-Benzolamide," *Bioorg. Med. Chem. Lett.* 14:5775-5780, 2004.

Cecchi et al., "Carbonic Anhydrase Inhibitors. Design of Fluorescent Sulfonamides as Probes of Tumor-Associated Carbonic Anhydrase IX That Inhibit Isozyme IX-Mediated Acidification of Hypoxic Tumors," *J. Med. Chem.* 48:4834-4841, 2005.

Chao et al., "Experimental Therapy with Tissue Kallikrein Against Cerebral Ischemia," *Front. Biosci.* 11:1323-1327, 2006.

Chen et al., "B2 Bradykinin Receptor Immunoreactivity in Rat Brain," *J. Comp. Neurol.* 427:1-18, 2000.

Chen et al., "MEK1,2 Response Element Mediates Angiotensin II-Stimulated Plasminogen Activator Inhibitor-1 Promoter Activation," *Blood* 103:2636-2644, 2004.

Chobanian et al., "The Seventh Report of the Joint National Committee on Prevention, Detection, Evaluation, and Treatment of High Blood Pressure: the JNC 7 Report," *JAMA* 289:2560-2572, 2003.

Cholewinski et al., "Identification of B2 Bradykinin Binding Sites on Cultured Cortical Astrocytes," *J. Neurochem.* 57:1456-1458, 1991.

Cichon et al., "Increased Activity of Coagulation Factor XII (Hageman Factor) Causes Hereditary Angioedema Type III," *Am. J. Human Genet.* 79:1098-1104, 2006.

Ciulla et al., "Diabetic Retinopathy and Diabetic Macular Edema: Pathophysiology, Screening, and Novel Therapies," *Diabetes Care* 26:2653-2664, 2003.

Clermont et al., "Carbonic Anhydrase I (CA-1) Induces Retinal Vascular Permability In Vivo Through the Bradykinin (BK)/Kallikrein Pathway," Annual Meeting of the Association for Research in Vision and Ophthalmology, Fort Lauderdale, FL, May 1-5, 2005, vol. 46, Suppl. S, p. 5183, 2005.

Clermont et al., "Role of Angiotensin II Type 1 Receptor in the Pathogenesis of Diabetic Retinopathy: Effects of Blood Pressure Control and Beyond," *J. Hypertens. Supply* 24:S73-80, 2006.

Dawson et al., "Pigment Epithelium-Derived Factor: A Potent Inhibitor of Angiogenesis," *Science* 285:245-248, 1999.

De La Cruz et al., "Pharmacological Approach to Diabetic Retinopathy," *Diabetes-Metabolism Res. Reviews* 20:91-113, 2004.

Demchuk et al., "Serum Glucose Level and Diabetes Predict Tissue Plasminogen Activator-Related Intracerebral Hemorrhage in Acute Ischemic Stroke," *Stroke* 30:34-39, 1999.

Dennis et al., "Long-Term Survival After First-Ever Stroke: the Oxfordshire Community Stroke Project," *Stroke* 24:796-800, 1993.

Dennis et al., "Potent and Selective Kunitz Domain Inhibitors of Plasma Kallikrein Designed by Phage Display," *J. Biol. Chem.* 270:25411-25417, 1995.

De Simoni et al., "Neuroprotection by Complement (C1) Inhibitor in Mouse Transient Brain Ischemia," *J. Cereb. Blood Flow. Metab.* 23:232-239, 2003.

Dewald et al., "Missense Mutations in the Coagulation Factor XII (Hageman Factor) Gene in Hereditary Angioedema With Normal C1 Inhibitor," *Biochem. Biophys. Res. Commun.* 343:1286-1289, 2006.

Dickneite, "Influence of C1-Inhibitor on Inflammation, Edema and Shock," *Behring. Inst. Mitt.* 93:299-305, 1993.

Dietrich et al., "CU-2010—A Novel Small Molecule Protease Inhibitor with Antifibrinolytic and Anticoagulant Properties," *Anesthesiology* 110:123-130, 2009.

(56) References Cited

OTHER PUBLICATIONS

Ding-Zhou et al., "LF 16-0687 Ms, a Bradykinin B2 Receptor Antagonist, Reduces Ischemic Brain Injury in a Murine Model of Transient Focal Cerebral Ischemia," *Br. J. Pharmacol.* 139:1539-1547, 2003.

Easton et al., "Bradykinin Increases Permeability by Calcium and 5-Lipoxygenase in the ECV304/C6 Cell Culture Model of the Blood-Brain Barrier," *Brain Res.* 953:157-169, 2002.

Ebrahimian et al., "Dual Effect of Angiotensin-Converting Enzyme Inhibition on Angiogenesis in Type 1 Diabetic Mice," *Arterioscler. Thromb. Vasc. Biol.* 25:65-70, 2005.

Ellis et al., "Inhibition of Bradykinin- and Kallikrein-Induced Cerebral Arteriolar Dilation by a Specific Bradykinin Antagonist," *Stroke* 18:792-795, 1987.

Emanueli et al., "Local Delivery of Human Tissue Kallikrein Gene Accelerates Spontaneous Angiogenesis in Mouse Model of Hindlimb Ischemia" *Circulation* 103:125-132, 2001.

Emanueli et al., "Targeting Kinin B(1) Receptor for Therapeutic Neovascularization," *Circulation* 105:360-366, 2002.

Feener et al., "Angiotensin II Induces Plasminogen Activator Inhibitor-1 and -2 Expression in Vascular Endothelial and Smooth Muscle Cells," *J. Clin. Invest.* 95:1353-1362, 1995.

Feener et al., "Role of Protein Kinase C in Glucose- and Angiotensin II-Induced Plasminogen Activator Inhibitor Expression," *Contrib. Nephrol.* 118:180-187, 1996.

Feener et al., "Vascular Dysfunction in Diabetes Mellitus," *Lancet* 1:S19-13, 1997.

Feener et al., "Endothelial Dysfunction in Diabetes Mellitus: Role in Cardiovascular Disease," *Heart Fail Monit.* 1:74-82, 2001.

Ferrara, "Vascular Endothelial Growth Factor: Basic Science and Clinical Progress," *Endocr. Rev.* 25:581-611, 2004.

Folli et al., "Angiotensin II Inhibits Insulin Signaling in Aortic Smooth Muscle Cells at Multiple Levels. A Potential Role for Serine Phosphorylation in Insulin/Angiotension II Crosstalk," *J. Clin. Invest.* 100:2158-2169, 1997.

Funatsu et al., "Angiotensin II and Vascular Endothelial Growth Factor in the Vitreous Fluid of Patients with Diabetic Macular Edema and Other Retinal Disorders," *Am. J. Ophthalmol.* 133:537-543, 2002.

Funatsu et al., "Vitreous Levels of Interleukin-6 and Vascular Endothelial Growth Factor Are Related to Diabetic Macular Edema," *Ophthalmology* 110:1690-1696, 2003.

Funatsu et al., "Vitreous Levels of Vascular Endothelial Growth Factor and Intercellular Adhesion Molecule 1 Are Related to Diabetic Macular Edema," *Ophthalmology* 1112:806-816, 2005.

Gao et al., "Kallikrein-Binding Protein Inhibits Retinal Neovascularization and Decreases Vascular Leakage," *Diabetologia* 46:689-698, 2003.

Gao et al., "Angiotensin II Stimulates Phosphorylation of an Ectodomain-Truncated Platelet-Derived Growth Factor Receptor-Beta and Its Binding to Class IA PI3K in Vascular Smooth Muscle Cells," *Biochem. J.* 397:337-344, 2006.

Gao et al., "Extracellular Carbonic Anhydrase Mediates Hemorrhagic Retinal and Cerebral Vascular Permeability Through Prekallikrein Activation," *Nat. Med.* 13:181-188, 2007.

Gao et al., "Characterization of the Vitreous Proteome in Diabetes Without Diabetic Retinopathy and Diabetes With Proliferative Diabetic Retinopathy," *J. Proteome Res.* 7:2516-2525, 2008.

Gao et al., "Angiotensin AT1 Receptor Antagonism Ameliorates Murine Retinal Proteome Changes Induced by Diabetes," *J. Proteome Res.* 8:5541-5549, 2009.

Garcia-Martin et al., "High Resolution pH(e) Imaging of Rat Glioma Using pH-Dependent Relaxivity," *Mag. Res. Med.* 55:309-315, 2006.

Gardner et al., "Astrocytes Increase Barrier Properties and ZO-1 Expression in Retinal Vascular Endothelial Cells," *Invest. Ophthalmol. Vis. Sci.* 38:2423-2427, 1997.

Giatromanolaki et al., "Expression of Hypoxia-Inducible Carbonic Anhydrase-9 Relates to Angiogenic Pathways and Independently to Poor Outcome in Non-Small Cell Lung Cancer," *Cancer Res.* 61:7992-7998, 2001.

Gimpl et al., "Bradykinin Receptors in Cultured Astrocytes from Neonatal Rat Brain Are Linked to Physiological Responses," *Neurosci. Lett.* 144:139-142, 1992.

Giusti et al., "Is Acetazolamide Effective in the Treatment of Diabetic Macular Edema? A Pilot Study," *Int. Ophthalmol.* 24:79-88, 2001.

Gonzalez et al., "Purification and Preliminary Characterization of a Plasma Kallikrein Inhibitor Isolated from Sea Hares *Aplysia dactylomela* Rang, 1828," *Toxicon* 43:219-223, 2004.

Gragoudas et al., "Pegaptanib for Neovascular Age-Related Macular Degeneration," *N. Engl. J. Med.* 351:2805-2816, 2004.

Griesbacher et al., "Involvement of Tissue Kallikrein but Not Plasma Kallikrein in the Development of Symptoms Mediated by Endogenous Kinins in Acute Pancreatitis in Rats," *Br. J. Pharmacol.* 137:692-700, 2002.

Hack et al., "Studies on the Contact System of Coagulation During Therapy with High Doses of Recombinant IL-2: Implications for Septic Shock," *Thromb. Haemost.* 65:497-503, 1991.

Hamajima et al., "Intranasal Administration of HIV-DNA Vaccine Formulated with a Polymer, Carboxymethylcellulose, Augments Mucosal Antibody Production and Cell-Mediated Immune Response," *Clin. Immunol. Immunopathol.* 88:205-210, 1998.

Hamdan et al., "Angiotensin-Converting Enzyme Inhibition Suppresses Plasminogen Activator Inhibitor-1 Expression in the Neointima of Balloon-Injured Rat Aorta," *Circulation* 93:1073-1078, 1996.

Han et al., "Increased Vascular Permeability in C1 Inhibitor-Deficient Mice Mediated by the Bradykinin Type 2 Receptor," *J. Clin. Invest.* 109:1057-1063, 2002.

Harris et al., "Soluble Tie2 and Flt1 Extracellular Domains in Serum of Patients with Renal Cancer and Response to Antiangiogenic Therapy," *Clin. Can. Res.* 7:1992-1997, 2001.

He et al., "Differential Regulation of Angiotensin II-Induced Expression of Connective Tissue Growth Factor by Protein Kinase C Isoforms in the Myocardium," *J. Biol. Chem.* 280:15719-15726, 2005.

Hess et al., "Cloning and Pharmacological Characterization of a Human Bradykinin (BK-2) Receptor," *Biochem. Biophys. Res. Commun.* 184:260-268, 1992.

Holder et al., "*Pseudomonas elastase* Acts as a Virulence Factor in Burned Hosts by Hageman Factor-Dependent Activation of the Host Kinin Cascade," *Infect. Immun.* 57:3345-3348, 1989.

Horio et al., "Angiotensin AT(1) Receptor Antagonism Normalizes Retinal Blood Flow and Acetylcholine-Induced Vasodilatation in Normotensive Diabetic Rats," *Diabetologia* 47:113-123, 2004.

Houle et al., "Tissue Kallikrein Actions at the Rabbit Natural or Recombinant Kinin B2 Receptors," *Hypertension* 41:611-617, 2003.

Howl et al., "Bradykinin Receptors as a Therapeutic Target," *Expert Opin. Ther. Targets* 7:277-285, 2003.

Igic, "Kallikrein and Kininases in Ocular Tissues," *Exp. Eye Res.* 41:117-120, 1985.

Imamura et al., "Induction of Vascular Leakage and Blood Pressure Lowering Through Kinin Release by a Serine Proteinase from *Aeromonas sobria*," *J. Immunol.* 177:8723-8729, 2006.

Innocenti et al. "Carbonic Anhydrase Inhibitors: The First On-Resin Screening of a 4-Sulfamoylphenylthiourea Library," *J. Med. Chem.* 47:5224-5229, 2004.

Isawa et al., "A Mosquito Salivary Protein Inhibits Activation of the Plasma Contact System by Binding to Factor XII and High Molecular Weight Kininogen," *J. Biol. Chem.* 277:27651-27658, 2002.

Ito et al., "Regulation of Blood Pressure by the Type 1A Angiotensin II Receptor Gene," *Proc. Natl. Acad. Sci. U.S.A.* 92:3521-3525, 1995.

Iwaki et al., "Plasma Levels of Bradykinin Are Suppressed in Factor XII-Deficient Mice," *Thromb. Haemost.* 95:1003-1010, 2006.

Janghorbani et al., "Prospective Study of Type 1 and Type 2 Diabetes and Risk of Stroke Subtypes:The Nurses' Health Study," *Diabetes Care* 30:1730-1735, 2007.

Jeppesen et al., "Bradykinin Relaxation in Small Porcine Retinal Arterioles," *Invest. Ophthalmol. Vis. Sci.* 43:1891-1896, 2002.

Joseph et al., "Heat Shock Protein 90 Catalyzes Activation of the Prekallikrein-Kininogen Complex in the Absence of Factor XII," *Proc. Natl. Acad. Sci. U.S.A.* 99:896-900, 2002.

Joseph et al., "Formation of Bradykinin: A Major Contributor to the Innate Inflammatory Response," *Adv. Immunol.* 86:159-208, 2005.

(56) References Cited

OTHER PUBLICATIONS

Kakoki et al., "Diabetic Nephropathy Is Markedly Enhanced in Mice Lacking the Bradykinin B2 Receptor," *Proc. Natl. Acad. Sci. U.S.A.* 101:13302-13305, 2004.

Kamitani et al., "Evidence for a Possible Role of the Brain Kallikrein-Kinin System in the Modulation of the Cerebral Circulation," *Circ. Res.* 57:545-552, 1985.

Kato et al., "Identification and Characterization of the Plasma Kallikrein-Kinin System Inhibitor, Haemaphysalin, from Hard Tick, *Haemaphysalis longicornis*," *Thromb. Haemost.* 93:359-367, 2005.

Kazui et al., "Predisposing Factors to Enlargement of Spontaneous Intracerebral Hematoma," *Stroke* 28:2370-2375, 1997.

Kent et al., "Macular Oedema: The Role of Soluble Mediators," *Br. J. Ophthalmol.* 84:542-545, 2000.

King et al., "Pigment-Epithelium-Derived Factor—A Key Coordinator of Retinal Neuronal and Vascular Functions," *N. Eng. J. Med.* 342:349-351, 2000.

Kissela et al., "Epidemiology of Ischemic Stroke in Patients with Diabetes: The Greater Cincinnati/Northern Kentucky Stroke Study," *Diabetes Care* 28:255-359, 2005.

Klein et al., "The Wisconsin Epidemiologic Study of Diabetic Retinopathy: XVII. The 14-Year Incidence and Progression of Diabetic Retinopathy and Associated Risk Factors in Type 1 Diabetes," *Ophthalmology* 105:1801-1815, 1998.

Kleinschnitz et al., "Targeting Coagulation Factor XII Provides Protection from Pathological Thrombosis in Cerebral Ischemia without Interfering with Hemostasis," *J. Exp. Med.* 203:513-518, 2006.

Knudsen et al., "Macular Edema Reflects Generalized Vascular Hyperpermeability in Type 2 Diabetic Patients with Retinopathy," *Diabetes Care* 25:2328-2334, 2002.

Krogsaa et al., "The Blood-Retinal Barrier Permeability in Diabetic Patients," *Acta. Ophthalmol.* (Copenh.) 59:689-694, 1981.

Kuznetsova et al., "Activity of Tissue and Plasma Kallikrein and Level of Their Precursors in Eye Tissue Structures and Media of Healthy Rabbits," *Vopr. Med. Khim.* 37:79-82, 1991. (Russian language article, English language abstract provided.).

Lamark et al., "Expression of Active Human C1 Inhibitor Serpin Domain in *Escherichia coli*," *Protein Expr. Purif.* 22:349-358, 2001.

Lathem et al., "Potentiation of C1 Esterase Inhibitor by StcE, a Metalloprotease Secreted by *Escherichia coli* O157:H7," *J. Exp. Med.* 199:1077-1087, 2004.

Lawson et al., "Enhanced Dermal and Retinal Vascular Permeability in Streptozotocin-Induced Type 1 Diabetes in Wistar Rats: Blockade with a Selective Bradykinin B1 Receptor Antagonist," *Regul. Pept.* 124:221-224, 2005.

Liao et al., "Expression of Cell Surface Transmembrane Carbonic Anhydrase Genes *CA9* and *CA12* in the Human Eye: Overexpression of *CA12* (CAXII) in Glaucoma," *J. Med. Genet.* 40:257-261, 2003.

Lin et al., "Inhibition of Nuclear Translocation of Transcription Factor NF-kappa B by a Synthetic Peptide Containing a Cell Membrane-Permeable Motif and Nuclear Localization Sequence," *J. Biol. Chem.* 270:14255-14258, 1995.

Liu et al., "Synergy Between A Plasminogen Cascade and MMP-9 in Autoimmune Disease," *J. Clin. Invest.* 115:879-887, 2005.

Lumenta et al., "Neuroprotective Effects of a Postischemic Treatment with a Bradykinin B2 Receptor Antagonist in a Rat Model of Temporary Focal Cerebral Ischemia," *Brain Res.* 1069:227-234, 2006.

Lund et al., "Plasminogen Activation Independent of uPA and tPA Maintains Wound Healing in Gene-Deficient Mice," *EMBO J.* 25:2686-2697, 2006.

Ma et al., "Expression and Cellular Localization of the Kallikrein-Kinin System in Human Ocular Tissues," *Exp. Eye Res.* 63:19-26, 1996.

Mahabeer et al., "Kallikrein and Kinin Receptor Genes," *Pharmacol. Ther.* 88:77-89, 2000.

Maier et al., "Intravitreal Injection of Specific Receptor Tyrosine Kinase Inhibitor PTK787/ZK222 584 Improves Ischemia-Induced Retinopathy in Mice," *Graefes Arch. Clin. Exp. Opthalmol.* 243:593-600, 2005.

Markland et al., "Iterative Optimization of High-Affinity Protease Inhibitors Using Phage Display. 2. Plasma Kallikrein and Thrombin," *Biochemistry* 35:8058-8067, 1996.

Marzouk et al., "Measurement of Extracellular pH, K(+), and Lactate in Ischemic Heart," *Anal. Biochem.* 308:52-60, 2002.

Matsuno et al., "Lack of Alpha 2-Antiplasmin Promotes Re-Endothelialization via Over-Release of VEGF After Vascular Injury in Mice," *Blood* 120:3621-3628, 2003.

Mayer et al., "Recombinant Activated Factor VII for Acute Intracerebral Hemorrhage," *N. Engl. J. Med.* 352:777-785, 2005.

Mayer et al., "Treatment of Intracerebral Haemorrhage," *Lancet Neurol.* 4:662-672, 2005.

Miao et al., "Structural Elements of Kallistatin Required for Inhibition of Angiogenesis," *Am. J. Physiol. Cell. Physiol.* 284:C1604-C1613, 2003.

Miller et al., "Vascular Endothelial Growth Factor/Vascular Permeability Factor Is Temporally and Spatially Correlated with Ocular Angiogenesis in a Primate Model," *Am. J. Pathol.* 145:574-584, 1994.

Miura et al., "Transactivation of KDR/Flk-1 by the B2 Receptor Induces Tube Formation in Human Coronary Endothelial Cells," *Hypertension* 41:1118-1123, 2003.

Miyamoto et al., "Prevention of Leukostasis and Vascular Leakage in Streptozotocin-Induced Diabetic Retinopathy Via Intercellular Adhesion Molecule-1 Inhibition," *Proc. Natl. Acad. Sci. U.S.A.* 96:10836-10841, 1999.

Morgan et al., "Carbonic Anhydrase Inhibitors That Directly Inhibit Anion Transport by the Human Cl-/HCO3-Exchanger, AE1," *Mol. Memb. Biol.* 21:423-433, 2004.

Nagelhus et al., "Carbonic Anhydrase XIV Is Enriched in Specific Membrane Domains of Retinal Pigment Epithelium, Muller Cells, and Astrocytes," *Proc. Natl. Acad. Sci. U.S.A.* 102:8030-8035, 2005.

Nakamura et al., "KRN633: A Selective Inhibitor of Vascular Endothelial Growth Factor Receptor-2 Tyrosine Kinase That Suppresses Tumor Angiogenesis and Growth," *Mol. Cancer Ther.* 3:1639-1649, 2004.

Nakanishi et al., "Catalogue of Soluble Proteins in the Human Vitreous Humor: Comparison Between Diabetic Retinopathy and Macular Hole," *J. Chromatogr. B Analyt. Tech. Biomed. Life Sci.* 776:89-100, 2002.

Nakazawa et al., "Inhibition of Contact Activation by a Kininogen Peptide (HKH20) Derived from Domain 5," *Int. Immunopharm.* 2:1875-1885, 2002.

Neaton et al., "Treatment of Mild Hypertension Study. Final Results. Treatment of Mild Hypertension Study Research Group," *JAMA* 270:713-724, 1993.

Ng et al., "MBD2 Is a Transcriptional Repressor Belonging to the MeCP1 Histone Deacetylase Complex," *Nat. Genet.* 23:58-61, 1999.

Ni et al., "Transcription Factor Nuclear Factor KappaB Regulates the Inducible Expression of the Human B1 Receptor Gene in Inflammation," *J. Biol. Chem.* 273:2784-2791, 1998.

Ni et al., "Overexpression of Kinin B1 Receptors Induces Hypertensive Response to des-Arg9-Bradykinin and Susceptibility to Inflammation," *J. Biol. Chem.* 278:219-225, 2003.

Nishikiori et al., "Glial Cell-Derived Cytokines Attenuate the Breakdown of Vascular Integrity in Diabetic Retinopathy," *Diabetes* 56:1333-1340, 2007.

Noda et al., "Expression and Function of Bradykinin Receptors in Microglia," *Life Sci.* 72:1573-1581, 2003.

Nussberger et al., "Plasma Bradykinin in Angio-Oedema," *Lancet* 351:1693-1697, 1998.

The NINDS t-PA Study Group, "Intracerebral Hemorrhage After Intravenous t-PA Therapy for Ischemic Stroke," *Stroke* 28:2109-2118, 1997.

Ogata et al., "Unbalanced Vitreous Levels of Pigment Epithelium-Derived Factor and Vascular Endothelial Growth Factor in Diabetic Retinopathy," *Am. J. Ophthalmol.* 134:348-353, 2002.

Ouchi et al., "Proteomic Analysis of Vitreous from Diabetic Macular Edema," *Exp. Eye. Res.* 81:176-182, 2005.

Pappalardo et al., "C1 Inhibitor Gene Expression in Patients with Hereditary Angioedema: Quantitative Evaluation by Means of Real-Time RT-PCR," *J. Allergy Clin. Immunol.* 114:638-644, 2004.

(56) References Cited

OTHER PUBLICATIONS

Pedersen et al., "Optic Nerve pH and PO2: The Effects of Carbonic Anhydrase Inhibition, and Metabolic and Respiratory Acidosis," *Acta. Ophthalmol. Scand.* 84:475-480, 2006.
Pelaez et al., "Low-Dose Angiotensin II Enhances Pressor Responses Without Causing Sustained Hypertension," *Hypertension* 42:798-801, 2003.
Pesquero et al., "Hypoalgesia and Altered Inflammatory Responses in Mice Lacking Kinin B1 Receptors," *Proc. Natl. Acad. Sci. U.S.A.* 97:8140-8145, 2000.
Phipps et al., "The Kallikrein-Kinin System in Diabetic Retinopathy: Lessons for the Kidney," *Kidney Int.* 73:1114-1119, 2008.
Pixley et al., "The Regulation of Human Factor XIIa by Plasma Proteinase Inhibitors," *J. Biol. Chem.* 260:1723-1729, 1985.
Plehwe et al., "Does Vitreous Fluorophotometry Reflect Severity of Early Diabetic Retinopathy?" *Br. J. Opthalmol.* 73:255-260, 1989.
Plesnila et al., "Role of Bradykinin B2 Receptors in the Formation of Vasogenic Brain Edema in Rats," *J. Neurotrauma* 18:1049-1058, 2001.
Quam et al., "VEGF-Initiated Blood-Retinal Barrier Breakdown in Early Diabetes," *Invest. Ophthalmol. Vis. Sci.* 42:2408-2413, 2001.
Qureshi et al., "Spontaneous Intracerebral Hemorrhage," *N. Engl. J. Med.* 344:1450-1460, 2001.
Raidoo et al., "Kinin Receptors on Human Neurons," *J. Neuroimmunol.* 77:39-44, 1997.
Raisler et al., "Adeno-associated Virus Type-2 Expression of Pigmented Epithelium-Derived Factor or Kringles 1-3 of Angiostatin Reduce Retinal Neovascularization," *Proc. Natl. Acad. Sci. U.S.A.* 99:8909-8914, 2002.
Reboul et al., "Proteolysis and Deglycosylation of Human C1 Inhibitor. Effect on Functional Properties," *Biochem. J.* 244:117-121, 1987.
Regoli et al., "B1 and B2 Kinin Receptors in Various Species," *Immunopharmacology* 36:143-147, 1997.
Regoli et al., "Receptors for Kinins: From Classical Pharmacology to Molecular Biology," *Immunopharmacology* 33:24-31, 1996.
Regoli et al., "Receptors for Kinins: From Classical Pharmacology to Molecular Biology," *Immunopharmacology* 33:116-122, 1996.
Relton et al., "CP-0597, A Selective Bradykinin B2 Receptor Antagonist, Inhibits Brain Injury in a Rat Model of Reversible Middle Cerebral Artery Occlusion," *Stroke* 28:1430-1436, 1997.
Rosamond et al., Heart Disease and Stroke Statistics—2007 Update: a Report from the American Heart Association Statistics Committee and Stroke Statistics Subcommittee, *Circulation* 115:e69-e171, 2007.
Sabourin et al., "Expression of Kinin B(1) Receptor in Fresh or Cultured Rabbit Aortic Smooth Muscle: Role of NF-Kappa B," *Am. J. Physiol. Heart Circ. Physiol.* 283:H227-H237, 2002.
Sasaki et al., "An Unexpected Inhibitory Activity of Kunitz-Type Serine Proteinase Inhibitor Derived from Boophilus Microplus Trypsin Inhibitor on Cathepsin L.," *Biochem. Biophys. Res. Commun.* 341:266-272, 2006.
Schneider et al., "Critical Role of Kallikrein in Hereditary Angioedema Pathogenesis: A Clinical Trial of Ecallantide, a Novel Kallikrein Inhibitor," *J. Allergy. Clin. Immunol.* 120:416-422, 2007.
Schoch et al., "Hypoxia-Induced Vascular Endothelial Growth Factor Expression Causes Vascular Leakage in the Brain," *Brain* 125:2549-2557, 2002.
Schousboe, "Binding of Activated Factor XII to Endothelial Cells Affects Its Inactivation by the C1-Esterase Inhibitor," *Eur. J. Biochem.* 270:111-118, 2003.
Schwaninger et al., "Bradykinin Induces Interleukin-6 Expression in Astrocytes Through Activation of Nuclear Factor-KappaB," *J. Neurochem.* 73:1461-1466, 1999.
Scott et al., "Kinetics of Inhibition of Human Plasma Kallikrein by a Site-Specific Modified Inhibitor Arg15-Aprotinin: Evaluation Using a Microplate System and Comparison with Other Proteases," *Blood* 69:1431-1436, 1987.
Scozzafava et al., "Carbonic Anhydrase Inhibitors: Synthesis of Sulfonamides Incorporating DTPA Tails and of Their Zinc Complexes with Powerful Topical Antiglaucoma Properties," *Bioorg. Med. Chem. Lett.* 11:575-582, 2001.
Selvarajan et al., "A Plasma Kallikrein-Dependent Plasminogen Cascade Required for Adipocyte Differentiation," *Nat. Cell Biol.* 3:267-275, 2001.
Shariat-Madar et al., "Identification and Characterization of Prolylcarboxypeptidase as an Endothelial Cell Prekallikrein Activator," *J. Biol. Chem.* 277:17962-17969, 2002.
Shariat-Madar et al., "Recombinant Prolylcarboxypeptidase Activates Plasma Prekallikrein," *Blood* 103:4554-4561, 2004.
Shariat-Madar et al., "Overexpression of Prolylcarboxypeptidase Enhances Plasma Prekallikrein Activation on Chinese Hamster Ovary Cells," *Am. J. Physiol. Heart Circ. Physiol.* 289:H2697-H2703, 2005.
Shia et al., "Conformational Lability in Serine Protease Active Sites: Structures of Hepatocyte Growth Factor Activator (HGFA) Alone and with the Inhibitory Domain from HGFA Inhibitor-1B," *J. Mol. Biol.* 346:1335-1349, 2005.
Shigematsu et al., "Bradykinin-Induced Proinflammatory Signaling Mechanisms," *Am. J. Physiol. Heart Circ. Physiol.* 283:H2676-H2686, 2002.
Siebeck et al., "Inhibition of Plasma Kallikrein with Aprotinin in Porcine Endotoxin Shock," *J. Trauma* 34:193-198, 1993.
Simo et al., "Free Insulin-Like Growth Factor 1 in the Vitreous Fluid of Diabetic Patients with Proliferative Diabetic Retinopathy: A Case-Control Study," *Clin. Sci.* (Lond.) 104:223-230, 2003.
Simo et al., "Hepatocyte Growth Factor in the Vitreous Fluid of Patients with Proliferative Diabetic Retinopathy: Its Relationship with Vascular Endothelial Growth Factor and Retinopathy Activity," *Diabetes Care* 27:287-288, 2004.
Sobey, "Bradykinin B2 Receptor Antagonism: A New Direction for Acute Stroke Therapy?" *Br. J. Pharmacol.* 139:1369-1371, 2003.
Song et al., "Hyperglycemia Exacerbates Brain Edema and Perihematomal Cell Death After Intracerebral Hemorrhage," *Stroke* 34:2215-2220, 2003.
Song et al., "Inhibition of Tumor Angiogenesis In Vivo by a Monoclonal Antibody Targeted to Domain 5 of High Molecular Weight Kininogen," *Blood* 104:2065-2072, 2004.
Spranger et al., "Release of the Angiogenesis Inhibitor Angiostatin in Patients with Proliferative Diabetic Retinopathy: Association with Retinal Photocoagulation," *Diabetologia* 43:1404-1407, 2000.
Srinivas et al., "Inhibition of Carbonic Anhydrase Activity in Cultured Bovine Corneal Endothelial Cells by Dorzolamide," *Invest. Opthalmol. Vis. Sci.* 43:3273-3278, 2002.
Stadnicki et al., "Selective Plasma Kallikrein Inhibitor Attenuates Acute Intestinal Inflammation in Lewis Rat," *Dig. Dis. Sci.* 41:912-920, 1996.
Stefansson et al., "Optic Nerve Oxygen Tension in Pigs and the Effect of Carbonic Anhydrase Inhibitors," *Invest. Ophthalmol. Vis. Sci.* 40:2756-2761, 1999.
Storini et al., "Selective Inhibition of Plasma Kallikrein Protects Brain from Reperfusion Injury," *J. Pharmacol. Exp. Ther.* 318:849-854, 2006.
Stratton et al., "Association of Glycaemia with Macrovascular and Microvascular Complications of Type 2 Diabetes (UKPDS 35): Prospective Observational Study," *BMJ* 321:405-412, 2000.
Sulikowski et al., "Alpha(1)-Proteinase Inhibitor Mutants with Specificity for Plasma Kallikrein and C1s but Not C1," *Protein Sci.* 11:2230-2236, 2002.
Sun et al., "Identification and Cloning of the $Na/HCO_3^-$ Transporter (NBC) in Human Corneal Epithelium," *Exp. Eye. Res.* 7:287-295, 2003.
Sun et al., "$HCO_3^-$-Dependent Soluble Adenylyl Cyclase Activates Cystic Fibrosis Transmembrane Conductance Regulator in Corneal Endothelium," *Am. J. Physiol. Cell Physiol.* 284:C1114-C1122, 2003.
Sun et al., "$[HCO_3^-]$-Regulated Expression and Activity of Soluble Adenylyl Cyclase in Corneal Endothelial and Calu-3 Cells," *BMC Physiol.* 4:8, 2004.
Supuran et al., "Carbonic Anhydrase Inhibitors," *Med. Res. Rev.* 23:146-189, 2003.

(56) References Cited

OTHER PUBLICATIONS

Suzuki et al., "Stromelysin-1 (MMP-3) Is Critical for Intracranial Bleeding After t-PA Treatment of Stroke in Mice," *J. Thromb. Haemost.* 5:1732-1739, 2007.
Suzuma et al., "Cyclic Stretch and Hypertension Induce Retinal Expression of Vascular Endothelial Growth Factor and Vascular Endothelial Growth Factor Receptor-2: Potential Mechanisms for Exacerbation of Diabetic Retinopathy by Hypertension," *Diabetes* 50:444-454, 2001.
Svastova et al., "Hypoxia Activates the Capacity of Tumor-Associated Carbonic Anhydrase IX to Acidify Extracellular pH," *FEBS Lett.* 577:439-445, 2004.
Tans et al., "Autoactivation of Human Plasma Prekallikrein," *J. Biol. Chem.* 262:11308-11314, 1987.
The Diabetes Control and Complications Trial Research Group, "The Effect of Intensive Treatment of Diabetes on the Development and Progression of Long-Term Complications in Insulin-Dependent Diabetes Mellitus. The Diabetes Control and Complications Trial Research Group," *N. Engl. J. Med.* 329:977-986, 1993.
Thuringer et al., "Rapid Transactivation of the Vascular Endothelial Growth Factor Receptor KDR/Flk-1 by the Bradykinin B2 Receptor Contributes to Endothelial Nitric-Oxide Synthase Activation in Cardiac Capillary Endothelial Cells," *J. Biol. Chem.* 277:2028-2032, 2002.
Tsuji et al., "Tissue Plasminogen Activator Promotes Matrix Metalloproteinase-9 Upregulation After Focal Cerebral Ischemia," *Stroke* 36:1954-1959, 2005.
Tuccillo et al., "Antitumor Activity of ZD6474, A Vascular Endothelial Growth Factor-2 and Epidermal Growth Factor Receptor Small Molecule Tyrosine Kinase Inhibitor, in Combination with SC-236, a Cyclooxygenase-2 Inhibitor," *Clin. Cancer Res.* 11:1268-1276, 2005.
UK Prospective Diabetes Study Group, "Tight Blood Pressure Control and Risk of Macrovascular and Microvascular Complications in Type 2 Diabetes: UKPDS 38," *BMJ* 37:703-713, 1998.
Unterberg et al., "Effects of Bradykinin on Permeability and Diameter of Pial Vessels In Vivo," *J. Cereb. Blood Flow. Metab.* 4:574-585, 1984.
van Doorn et al., "A Phase I Study of Recombinant Human C1 Inhibitor in Asymptomatic Patients with Hereditary Angioedema," *J. Allergy Clin. Immunol.* 116:876-883, 2005.
van Nieuw Amerongen Geerten et al., "Targets for Pharmacological Intervention of Endothelial Hyperpermeability and Barrier Function," *Vascular Pharmacol.* 39:257-272, 2002.
Veloso et al., "A Monoclonal Anti-Human Plasma Prekallikrein Antibody That Inhibits Activation of Prekallikrein by Factor XIIa on a Surface," *Blood* 70:1053-1062, 1987.
Verheul, "Vascular Endothelial Growth Factor and Its Inhibitors," *Drugs Today* (Barc.) 39 Suppl. C:81-93, 2003.
Vorstrup et al., "Effect of Acetazolamide on Cerebral Blood Flow and Cerebral Metabolic Rate for Oxygen," *J. Clin. Invest.* 74:1634-1639, 1984.
Wagner et al., "Activation of the Tissue Kallikrein-Kinin System in Stroke," *J. Neurol. Sci.* 202:75-76, 2002.
Weber et al., "Unexpected Nanomolar Inhibition of Carbonic Anhydrase by COX-2-Selective Celecoxib: New Pharmacological Opportunities due to Related Binding Site Recognition," *J. Med. Chem.* 47:550-557, 2004.
Wilkinson-Berka, "Angiotensin and Bradykinin: Targets for the Treatment of Vascular and Neuro-Glial Pathology in Diabetic Retinopathy," *Curr. Pharm. Des.* 10:3313-3330, 2004.
Wilkinson-Berka, "Vasoactive Factors and Diabetic Retinopathy: Vascular Endothelial Growth Factor, Cyclooxygenase-2 and Nitric Oxide," *Curr. Pharm. Des.* 10:3331-3348, 2004.
Williams et al., "Epidemiology of Diabetic Retinopathy and Macular Oedema: A Systematic Review," *Eye* (Lond). 18:963-983, 2004.
Winum et al., "Carbonic Anhydrase Inhibitors: Inhibition of Transmembrane, Tumor-Associated Isozyme IX, and Cytosolic Isozymes I and II with Aliphatic Sulfamates," *J. Med. Chem.* 46:5471-5477, 2003.

Wistrand et al., "Carbonic Anhydrase Isoenzymes CA I and CA II in the Human Eye," *Invest. Opthalmol. Vis. Sci.* 27:419-428, 1986.
Wojtkowski et al., "Three-Dimensional Retinal Imaging with High-Speed Ultrahigh-Resolution Optical Coherence Tomography," *Ophthalmology* 112:1734-1746, 2005.
Wolfensberger et al., "Membrane-Bound Carbonic Anhydrase in Human Retinal Pigment Epithelium," *Invest. Ophthalmol. Vis. Sci.* 35:3401-3407, 1994.
Wolfensberger, "The Role of Carbonic Anhydrase Inhibitors in the Management of Macular Edema," *Documenta Ophthalmologica* 97:387-397, 1999.
Xi et al., "Mechanisms of Edema Formation After Intracerebral Hemorrhage: Effects of Extravasated Red Blood Cells on Blood Flow and Blood-Brain Barrier Integrity," *Stroke* 32:2932-2938, 2001.
Xia et al., "Kallikrein Protects Against Ischemic Stroke by Inhibiting Apoptosis and Inflammation and Promoting Angiogenesis and Neurogenesis," *Hum. Gene. Ther.* 17:206-219, 2006.
Xia et al., "Postischemic Brain Injury Is Exacerbated in Mice Lacking the Kinin B2 Receptor," *Hypertension* 47:752-761, 2006.
Yamane et al., "Proteome Analysis of Human Vitreous Proteins," *Mol. Cell. Proteomics* 2:1177-1187, 2003.
Yang et al., "Mutant Carbonic Anhydrase 4 Impairs pH Regulation and Causes Retinal Photoreceptor Degeneration," *Hum. Mol. Genet.* 14:255-265, 2005.
Yanyali et al., "Bevacizumab (Avastin) for Diabetic Macular Edema in Previously Vitrectomized Eyes," *Am. J. Ophthalmol.* 144:124-126, 2007.
Zahedi et al., "Unique C1 Inhibitor Dysfunction in a Kindred Without Angioedema. II. Identification of an Ala443→ Val Substitution and Functional Analysis of the Recombinant Mutant Protein," *J. Clin. Invest.* 95:1299-1305, 1995.
Zahedi et al., "C1 Inhibitor: Analysis of the Role of Amino Acid Residues Within the Reactive Center Loop in Target Protease Recognition," *J. Immunol.* 167:1500-1506, 2001.
Zhou et al., "Kallistatin: A Novel Human Tissue Kallikrein Inhibitor. Purification, Characterization, and Reactive Center Sequence," *J. Biol. Chem.* 267:25873-25880, 1992.
Supplemental European Search Report and European Search Opinion for EP 06735178, search completed Jul. 9, 2009, search and opinion mailed Jul. 20, 2009.
International Search Report for PCT/US06/005395, completed Jun. 11, 2008, mailed Jul. 14, 2008.
International Search Report for PCT/US08/00998, completed Aug. 6, 2008, mailed Aug. 11, 2008.
International Search Report for PCT/US09/00609, completed Mar. 28, 2009, mailed Apr. 13, 2009.
International Search Report for PCT/US09/66437, completed Jan. 18, 2010, mailed Feb. 3, 2010.
International Preliminary Report on Patentability for PCT/US06/005395, issued Mar. 10, 2009.
International Preliminary Report on Patentability for PCT/US08/00998, issued Jul. 28, 2009.
Written Opinion of the International Searching Authority for PCT/US06/005395, completed Jun. 11, 2008, mailed Jul. 14, 2008.
Written Opinion of the International Searching Authority for PCT/US08/00998, completed Aug. 6, 2008, mailed Aug. 11, 2008.
Written Opinion of the International Searching Authority for PCT/US09/00609, completed Mar. 28, 2009, mailed Apr. 13, 2009.
Written Opinion of the International Searching Authority for PCT/US09/66437, completed Jan. 18, 2010, mailed Feb. 3, 2010.
Holter et al., J. Clin. Invest. 78:1513-22 (1986).
Nagy et al., Angiogenesis 11:109-19 (2008).
Zhang et al., Arch. Dermatol. Res. 297:425-29 (2006).
Carvalho et al., J. Clin. Immunol. 27:246-56 (2007).
Senger et al., Science 219:983-85 (1983).
Wang et al., J. Infect. Dis. 202:991-1001 (2010).
Hamano et al., J. Biol. Chem. 277:31154-62 (2002).
Kramer et al., Kidney Int'l. 55:2362-67 (1999).
Villasante et al., J. Clin. Endocrinol. Metab. 92:314-321 (2007).
Pickkers et al., Shock 24:508-12 (2005).
Mulligan et al., Am. J. Pathol. 144:1008-15 (1994).
Chen HC et al., Arterioscler Thromb Vasc Biol. 20(10):2297-302 (2000).

(56) References Cited

OTHER PUBLICATIONS

Moreau et al., J Pharmacol Sci. 99:6-38 (2005).
Phipps JA et al., Hypertension. 53(2):175-81 (2009).
Chakravarty S. et al., J Mol Biol. 243(2):298-309 (1994).
Tsuda Y. et al., Chem Pharm Bull (Tokyo) 46(3):452-7 (1998).
Witkin SR et al., JAMA. 251(19):2534-7 (1984).
Kita and Feener, "Kallikrein-kinin system in the eye," M. Bader (Ed). In: *Kinins*. New York: Walter de Gruyter GmbH & Co. KG; Chapter 11, pp. 171-186, Aug. 19, 2011.

* cited by examiner

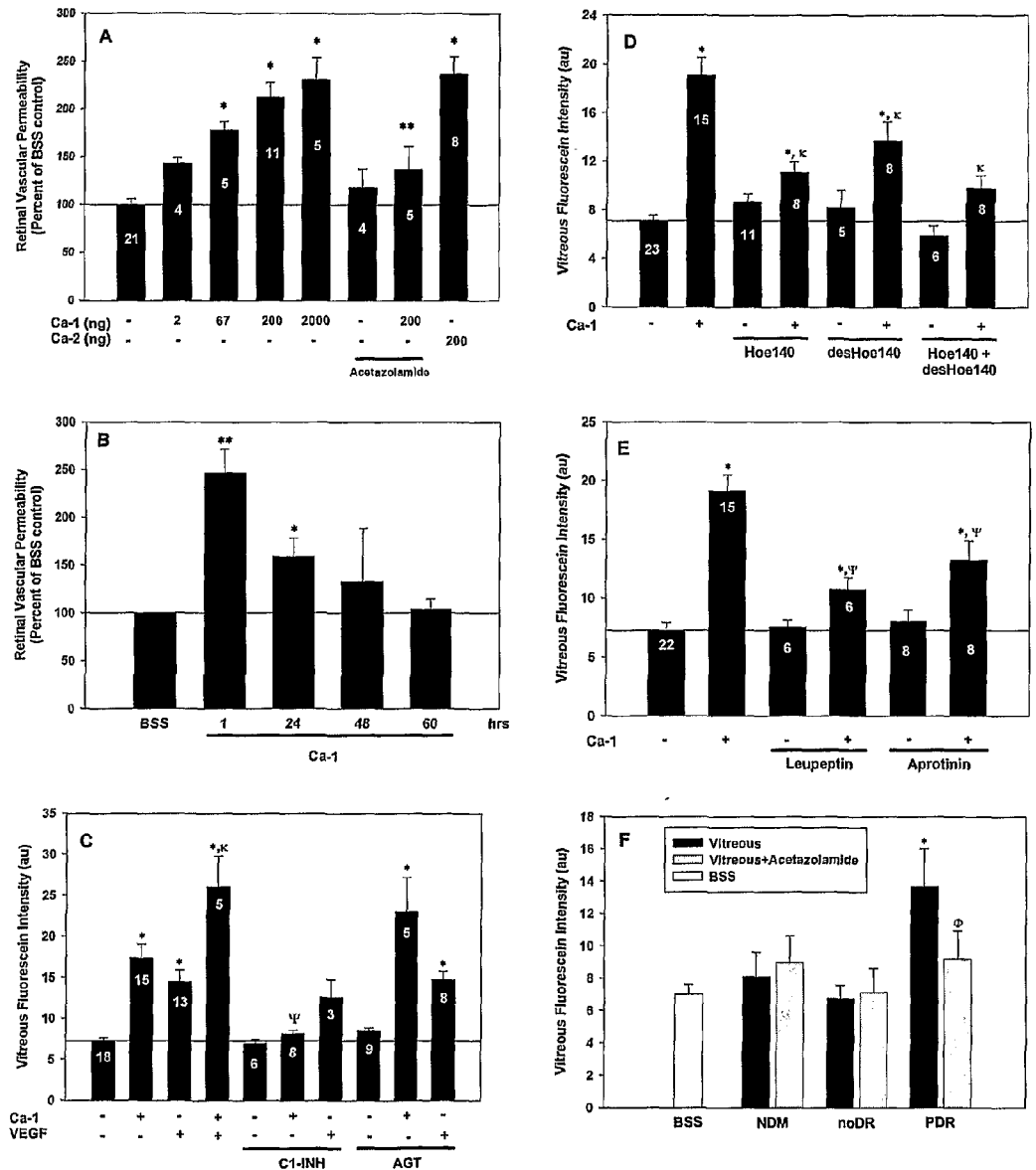
Figures 3A-F

| Protein Name | Accession | All Subjects (n = 13) | | | | NDM Only (n = 5) | | | | DM Only (n = 3) | | | | PDR Only (n = 3) | | | | Group Differences | |
|---|---|---|---|---|---|---|---|---|---|---|---|---|---|---|---|---|---|---|---|
| | | Range | Median | Mean | ± SD | Range | Median | Mean | ± SD | Range | Median | Mean | ± SD | Range | Median | Mean | ± SD | Chi-Square | P value |
| Complement C1q C chain | 20178281 | 0 - 4 | 0.0 | 0.6 | ±1.4 | 0 - 0 | 0 | 0.0 | ±0.0 | 0 - 4 | 0.0 | 1.0 | ±2.0 | 0 - 3 | 0.0 | 1.0 | ±1.7 | 1.57 | 0.26 |
| complement C4B | 13142244 | 0 - 33 | 15.0 | 16.2 | ±8.8 | 5 - 15 | 5 | 8.4 | ±4.8 | 11 - 33 | 22.0 | 22.0 | ±8.0 | 15 - 33 | 16.0 | 21.3 | ±10.1 | 8.08 *** | 0.05 |
| complement component 1 inhibitor | 156285894 | 0 - 17 | 7.0 | 8.5 | ±4.4 | 3 - 7 | 5 | 5.4 | ±1.5 | 7 - 14 | 12.5 | 11.5 | ±3.1 | 5 - 17 | 7.0 | 9.7 | ±6.4 | 5.14 | 0.08 |
| complement component 2 [1,2] | 14553437 | 0 - 4 | 0.0 | 0.6 | ±1.4 | 3 - 7 | 5 | 5.4 | ±1.5 | 0 - 0 | 0.0 | 0.0 | ±0.0 | 0 - 4 | 0.0 | 1.3 | ±2.3 | 1.75 | 0.42 |
| complement component 3 [1,2] | 437987791 | 0 - 60 | 24.0 | 27.3 | ±14.6 | 14 - 26 | 15 | 17.6 | ±4.8 | 13 - 60 | 30.0 | 33.3 | ±20.2 | 27 - 46 | 34.0 | 35.7 | ±9.6 | 4.07 | 0.13 |
| complement component 6 [1,2] | 38488662 | 0 - 4 | 0.0 | 0.5 | ±1.2 | 0 - 0 | 0 | 0.0 | ±0.0 | 0 - 4 | 0.0 | 1.0 | ±2.0 | 0 - 2 | 0.0 | 0.7 | ±1.2 | 1.57 | 0.46 |
| complement component 8 | 40557393 | 0 - 6 | 0.0 | 1.3 | ±2.4 | 0 - 0 | 0 | 0.0 | ±0.0 | 0 - 6 | 2.5 | 2.5 | ±2.9 | 0 - 6 | 0.0 | 2.0 | ±3.5 | 2.81 | 0.27 |
| complement component 9 [1,2] | 4502511 | 0 - 6 | 1.5 | 2.0 | ±1.9 | 0 - 0 | 0 | 0.0 | ±0.0 | 0 - 5 | 1.0 | 1.3 | ±2.5 | 3 - 5 | 5.0 | 4.1 | ±1.2 | 7.15 ** | 0.03 |
| Complement factor B | 5944306 | 0 - 12 | 3.0 | 3.4 | ±4.0 | 0 - 4 | 0 | 1.2 | ±1.9 | 0 - 8 | 5.0 | 4.5 | ±3.8 | 0 - 12 | 4.0 | 5.3 | ±6.1 | 2.61 | 0.27 |
| complement factor D [2] | 42544238 | 0 - 3 | 0.0 | 0.8 | ±1.1 | 0 - 2 | 0 | 0.4 | ±0.9 | 0 - 3 | 0.0 | 1.0 | ±1.5 | 0 - 3 | 2.0 | 1.7 | ±1.5 | 4.19 | 0.13 |
| complement factor H [1,2] | 45243375 | 0 - 10 | 0.0 | 1.8 | ±3.7 | 0 - 0 | 0 | 0.0 | ±0.0 | 0 - 0 | 0.0 | 0.0 | ±0.0 | 0 - 10 | 2.0 | 3.7 | ±4.7 | 3.39 | 0.18 |
| complement factor I [2] | 13355056 | 0 - 8 | 2.0 | 2.1 | ±2.4 | 0 - 2 | 0 | 0.4 | ±0.9 | 0 - 10 | 3.0 | 2.5 | ±5.0 | 2 - 8 | 2.0 | 4.3 | ±3.2 | 5.83 | 0.05 |
| Corticosteroid binding globulin | 330034181 | 0 - 4 | 0.0 | 0.8 | ±1.3 | 0 - 4 | 0 | 0.8 | ±0.9 | 0 - 4 | 3.0 | 2.5 | ±1.9 | 0 - 4 | 2.0 | 2.0 | ±2.0 | 2.44 | 0.30 |
| crystallin, alpha A | 4503056 | 0 - 4 | 0.0 | 0.9 | ±1.7 | 0 - 5 | 0 | 0.0 | ±0.0 | 0 - 2 | 0.0 | 0.5 | ±1.0 | 0 - 4 | 2.0 | 1.0 | ±1.7 | 2.35 | 0.23 |
| cystatin C | 4503107 | 0 - 8 | 4.0 | 3.8 | ±1.6 | 3 - 5 | 4 | 3.4 | ±1.0 | 0 - 5 | 4.0 | 3.8 | ±2.4 | 5 - 8 | 5.0 | 4.7 | ±1.5 | 1.28 | 0.53 |
| deltaglobin [1,2] | 16462105 | 0 - 8 | 6.0 | 5.3 | ±3.4 | 4 - 8 | 4 | 5.0 | ±1.8 | 3 - 8 | 8.0 | 6.3 | ±4.0 | 6 - 8 | 6.0 | 6.3 | ±1.5 | 8.83 ** | 0.04 |
| desmoplakin | 47755200 | 0 - 5 | 0.0 | 1.3 | ±2.0 | 0 - 3 | 0 | 0.6 | ±1.2 | 0 - 4 | 0.0 | 1.3 | ±2.3 | 0 - 6 | 2.0 | 2.0 | ±2.0 | 1.10 | 0.58 |
| Dickkopf related protein-3 | 13132491 | 0 - 6 | 3.0 | 2.5 | ±2.2 | 2 - 5 | 4 | 3.6 | ±1.1 | 0 - 2 | 2.0 | 1.3 | ±1.1 | 0 - 3 | 2.0 | 1.0 | ±1.7 | 2.77 | 0.25 |
| enolase 1 | 4503571 | 0 - 4 | 2.0 | 1.7 | ±1.6 | 0 - 4 | 0 | 0.7 | ±0.9 | 0 - 3 | 2.0 | 1.8 | ±0.9 | 0 - 4 | 0.0 | 1.3 | ±2.3 | 1.85 | 0.44 |
| Fibrinogen alpha chain [1,2] | 117616329 | 0 - 5 | 0.0 | 0.8 | ±1.6 | 0 - 0 | 0 | 0.0 | ±0.0 | 0 - 5 | 0.0 | 1.3 | ±2.5 | 0 - 5 | 0.0 | 1.3 | ±2.3 | 1.57 | 0.46 |
| Fibrinogen beta chain [1,2] | 117616331 | 0 - 10 | 3.0 | 3.1 | ±3.0 | 0 - 5 | 0 | 1.4 | ±2.1 | 2 - 10 | 2.0 | 4.5 | ±5.0 | 5 - 13 | 9.0 | 6.7 | ±4.0 | 4.07 | 0.13 |
| Fibrinogen gamma chain [1] | 117616333 | 0 - 7 | 1.0 | 1.8 | ±2.6 | 0 - 2 | 0 | 0.8 | ±1.1 | 0 - 5 | 0.0 | 2.3 | ±3.1 | 0 - 7 | 2.0 | 3.0 | ±3.6 | 0.97 | 0.62 |
| fluxepeden | 1429997 | 0 - 13 | 1.0 | 3.8 | ±4.7 | 0 - 2 | 0 | 0.4 | ±1.1 | 0 - 13 | 6.5 | 7.5 | ±6.4 | 0 - 9 | 5.0 | 4.7 | ±4.5 | 4.29 | 0.12 |
| fibulin 1 | 108837 | 0 - 2 | 0.0 | 0.3 | ±1.0 | 0 - 2 | 0 | 1.2 | ±0.9 | 0 - 0 | 0.0 | 0.0 | ±0.0 | 0 - 0 | 0.0 | 0.0 | ±0.0 | 2.70 | 0.26 |
| galectin 7 | 4504985 | 0 - 3 | 0.0 | 0.7 | ±1.2 | 0 - 0 | 0 | 0.0 | ±0.0 | 0 - 3 | 2.5 | 2.0 | ±1.5 | 0 - 3 | 2.0 | 1.7 | ±1.5 | 3.69 | 0.16 |
| Galectin-3 binding protein | 50311663 | 0 - 8 | 0.0 | 0.7 | ±1.2 | 0 - 3 | 0 | 0.8 | ±1.3 | 0 - 5 | 0.0 | 2.0 | ±4.4 | 0 - 8 | 8.0 | 8.0 | ±0.0 | 7.20 ** | 0.03 |
| GAPDH [3] | 31645 | 0 - 6 | 0.0 | 1.3 | ±2.0 | 2 - 6 | 3 | 3.4 | ±1.6 | 0 - 2 | 0.5 | 0.6 | ±1.0 | 2 - 7 | 4.0 | 4.0 | ±2.5 | 6.77 ** | 0.03 |
| gelsolin isoform a | 45204165 | 0 - 18 | 8.5 | 7.8 | ±4.2 | 3 - 9 | 5 | 4.2 | ±1.1 | 6 - 14 | 9.5 | 8.8 | ±3.3 | 7 - 15 | 10.0 | 11.0 | ±4.8 | 8.35 ** | 0.02 |
| glutathione peroxidase | 218031980 | 0 - 13 | 5.0 | 6.2 | ±2.9 | 2 - 5 | 4 | 4.4 | ±1.6 | 4 - 10 | 7.0 | 7.0 | ±2.5 | 5 - 13 | 6.0 | 8.0 | ±4.4 | 4.48 | 0.11 |
| glutathione transferase | 4504183 | 0 - 2 | 0.0 | 0.3 | ±0.8 | 0 - 2 | 0 | 0.4 | ±0.9 | 0 - 2 | 0.0 | 0.8 | ±1.5 | 0 - 0 | 0.0 | 0.7 | ±1.2 | 1.85 | 0.44 |
| haptoglobin [2] | 4826762 | 0 - 15 | 0.0 | 4.1 | ±6.1 | 0 - 0 | 0 | 0.0 | ±0.0 | 0 - 2 | 0.0 | 1.3 | ±1.5 | 0 - 15 | 3.0 | 8.0 | ±7.9 | 5.25 | 0.07 |
| Heat shock protein 27kDa protein 1 | 4504517 | 0 - 3 | 0.0 | 0.4 | ±1.0 | 0 - 2 | 0 | 0.4 | ±0.9 | 0 - 3 | 0.0 | 1.5 | ±1.0 | 0 - 2 | 0.0 | 0.7 | ±1.2 | 1.57 | 0.46 |
| Heat shock protein HSP 90-beta | 201485464 | 0 - 3 | 0.0 | 0.4 | ±1.0 | 0 - 0 | 0 | 0.0 | ±0.0 | 0 - 0 | 0.0 | 0.0 | ±0.0 | 0 - 0 | 0.0 | 0.0 | ±0.0 | 4.36 | 0.11 |
| hemoglobin alpha-1 globin chain [1,2] | 13850074 | 0 - 10 | 9.0 | 3.4 | ±4.4 | 0 - 9 | 0 | 3.4 | ±2.6 | 4 - 10 | 2.5 | 3.5 | ±4.4 | 8 - 10 | 9.0 | 9.0 | ±0.0 | 7.62 ** | 0.02 |
| Hemopexin | 13560068 | 0 - 10 | 4.5 | 5.1 | ±2.2 | 0 - 0 | 4 | 4.2 | ±1.3 | 4 - 10 | 5.5 | 6.3 | ±2.9 | 2 - 7 | 6.0 | 5.0 | ±2.6 | 1.61 | 0.49 |
| histidine-rich glycoprotein | 4504489 | 0 - 5 | 1.0 | 1.5 | ±1.5 | 0 - 5 | 0 | 0.4 | ±0.9 | 0 - 2 | 2.0 | 2.3 | ±1.1 | 0 - 4 | 3.0 | 2.3 | ±2.1 | 3.39 | 0.19 |
| inter-alpha (globulin) inhibitor H1 | 4504781 | 0 - 10 | 2.0 | 2.0 | ±3.5 | 0 - 0 | 0 | 0.0 | ±0.0 | 0 - 0 | 0.0 | 0.0 | ±0.0 | 0 - 2 | 0.0 | 0.7 | ±1.2 | 5.86 | 0.05 |
| inter-alpha (globulin) inhibitor H2 | 4504783 | 0 - 9 | 1.0 | 1.8 | ±2.6 | 0 - 0 | 0 | 1.0 | ±1.4 | 0 - 3 | 3.0 | 3.5 | ±1.3 | 0 - 2 | 1.0 | 1.0 | ±1.7 | 2.46 | 0.29 |
| M heavy chain 14 [1,2] | 10835547 | 0 - 17 | 1.0 | 3.8 | ±5.8 | 0 - 2 | 0 | 0.4 | ±0.9 | 0 - 17 | 3.0 | 5.8 | ±8.8 | 3 - 14 | 6.7 | 6.7 | ±8.4 | 4.44 | 0.10 |
| kininogen [1,2] | 395652 | 0 - 5 | 0.0 | 1.0 | ±2.0 | 0 - 0 | 0 | 0.0 | ±0.0 | 0 - 0 | 0.0 | 0.0 | ±0.0 | 0 - 5 | 2.0 | 2.3 | ±2.5 | 3.69 | 0.16 |
| leucine-rich alpha-2-glycoprotein 1 [1,2] | 16418467 | 0 - 5 | 0.0 | 1.5 | ±2.0 | 0 - 0 | 0 | 0.0 | ±0.0 | 0 - 3 | 1.5 | 1.5 | ±1.7 | 3 - 5 | 3.0 | 4.0 | ±1.7 | 7.56 ** | 0.02 |
| lumican | 4505047 | 0 - 3 | 0.0 | 0.5 | ±1.2 | 0 - 3 | 0 | 0.9 | ±1.5 | 0 - 0 | 0.0 | 0.0 | ±0.0 | 0 - 3 | 1.0 | 1.0 | ±1.7 | 1.65 | 0.44 |
| Metalloproteinase inhibitor 2 | 4507511 | 0 - 3 | 0.0 | 0.5 | ±1.2 | 0 - 0 | 0 | 0.0 | ±0.0 | 0 - 0 | 0.0 | 0.0 | ±0.0 | 0 - 3 | 0.0 | 1.0 | ±1.7 | 1.65 | 0.44 |
| myosin VA | 108839319 | 0 - 7 | 1.5 | 2.5 | ±2.8 | 0 - 7 | 5 | 4.6 | ±2.7 | 0 - 0 | 0.0 | 0.0 | ±0.0 | 0 - 4 | 3.5 | 2.3 | ±2.1 | 6.17 * | 0.05 |

Figure 4C

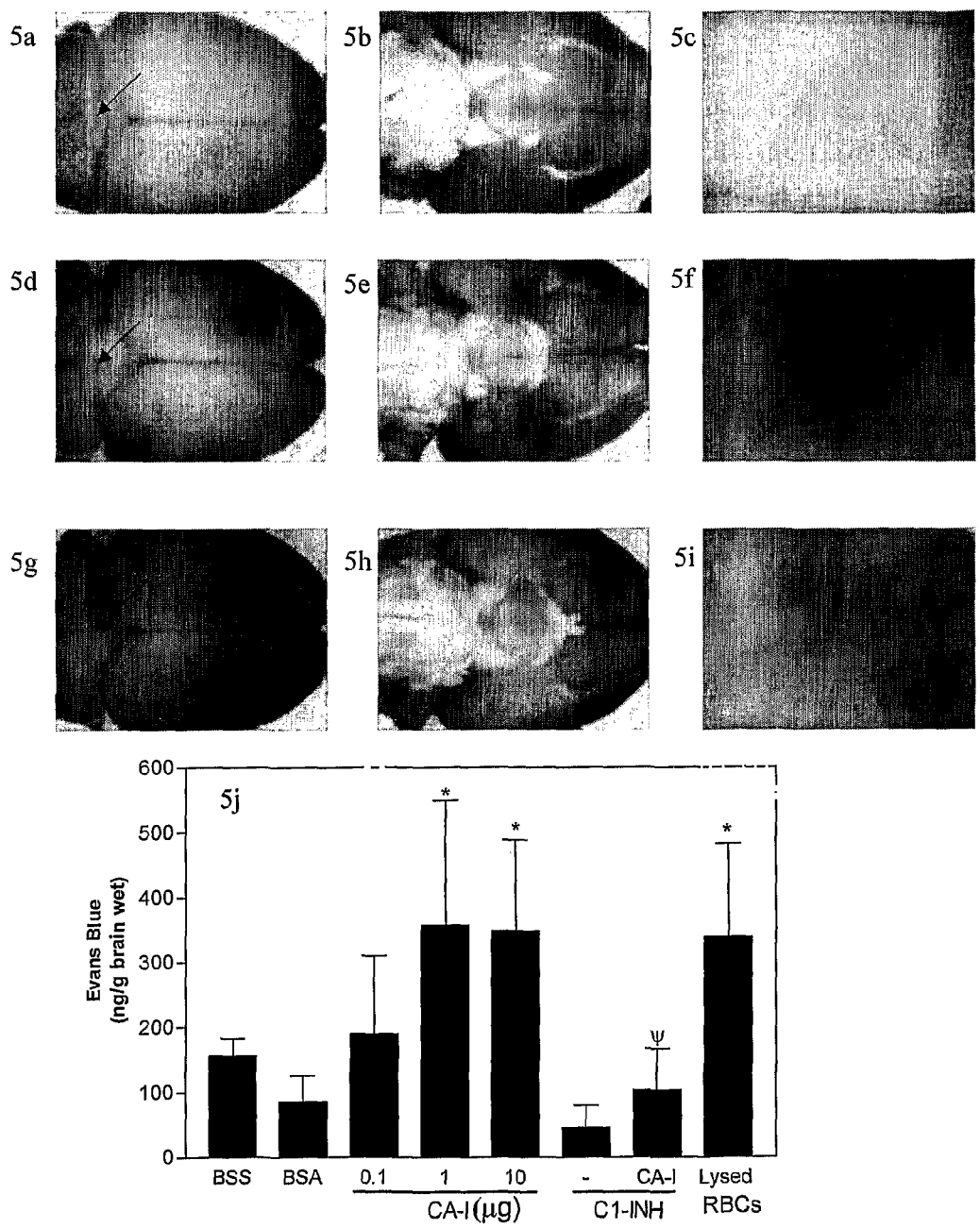
Fig. 5A-J

SEQUENCE LISTING

<160> NUMBER OF SEQ ID NOS: 1

<210> SEQ ID NO 1
<211> LENGTH: 60
<212> TYPE: PRT
<213> ORGANISM: Artificial Sequence
<220> FEATURE:
<223> OTHER INFORMATION: DX-88

<400> SEQUENCE: 1

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

COMPOSITIONS AND METHODS FOR TREATING VASCULAR PERMEABILITY

CLAIM OF PRIORITY

This application is the U.S. National Stage of International Application No. PCT/US2006/005395, filed Feb. 16, 2006, which claims the benefit of U.S. Provisional Patent Applications Ser. Nos. 60/656,167, filed on Feb. 24, 2005, and 60/725,820, filed on Oct. 12, 2005. The entire contents of these applications are hereby incorporated by reference.

FEDERALLY SPONSORED RESEARCH OR DEVELOPMENT

This invention was made with U.S. Government support under Grant Nos. RO1-EY11289-16, R01-EY13178, P30-EY13078, EY014106, DK 60165 and DK 36836, awarded by the National Institutes of Health. The U.S. Government has certain rights in the invention.

INCORPORATION BY REFERENCE OF A SEQUENCE LISTING FILED ELECTRONICALLY

Kindly incorporate the .txt file Sequence Listing, submitted Nov. 18, 2010, having the name 50339_004003_Sequence_Listing_ST25.txt, file size 0.99 kB, created on Nov. 17, 2010.

TECHNICAL FIELD

This invention relates to compounds and methods for diagnosing and treating disorders associated with excessive vascular permeability and edema, e.g., in the retina and brain.

BACKGROUND

The control of vascular permeability is essential for maintenance of normovolemia, most importantly in constrained spaces of the body such as the eye and the brain. Vasogenic cerebral edema arises from transvascular leakage caused by mechanical failure or dysfunction of the endothelial tight junctions of the blood-brain barrier (BBB), and is characterized by an increase in extracellular fluid volume due to the increased permeability of brain capillary endothelial cells to macromolecular serum proteins (e.g., albumin). Under normal physiological conditions, the entry of plasma protein-containing fluid into the extracellular space is limited by endothelial cell tight junctions. However, in the presence of massive injury there is increased permeability of brain capillary endothelial cells. Vasogenic edema can displace the brain hemisphere; severe edema can lead to cerebral herniation and contribute to neuronal cell death. Vasogenic edema is often associated with subdural hemorrhage (e.g., from a cranial injury) and hemorrhagic stroke.

Diabetic retinopathy (DR) is the leading cause of vision loss in working adults (Klein et al., Opthalmology 105:1801-1815 (1998); Ciulla et al., Diabetes Care 26:2653-2664 (2003)). Although its incidence and progression can be reduced by intensive glycemic and blood pressure control (The Diabetes Control and Complications Trial Research Group, N. Engl. J. Med. 329:977-986 (1993); Stratton et al., BMJ 321:405-412 (2000); UK Prospective Diabetes Study Group BMJ. 317:703-713 (1998) [published erratum appears in BMJ 1999 Jan. 2; 318(7175):29]), nearly all patients with type 1 diabetes mellitus (DM) and over 60% of those with type 2 DM develop retinal microvascular abnormalities termed nonproliferative diabetic retinopathy (NPDR), and 20% to 30% of these patients advance to active proliferative diabetic retinopathy (PDR) and/or diabetic macular edema (DME) (Aiello et al., Diabetes Care 21:143-156 (1998); Klein et al., Opthalmology 91:1464-1474 (1984); Javitt et al. Diabetes Care 17:909-917 (1994); Williams et al., Eye 18:963-983 (2004)). While photocoagulation surgery and vitrectomy are highly effective in reducing vision loss, preventative treatments for PDR and DME remain a major unmet clinical need.

Increased retinal vascular permeability (RVP) is a primary cause of DME and a characteristic finding in PDR, as well as other disorders. The retinal vascular barrier has an essential role in maintaining the composition of both of retinal interstitial fluid and the vitreous humor. An increase in RVP occurs in early diabetes and the magnitude of RVP correlates with the severity of DR (Krogsaa et al., Acta Opthalmol. (Copenh.) 59:689-694 (1981); Plehwe et al., Br. J. Opthalmol. 73:255-260 (1989); Lattanzio et al., Eur. J. Opthalmol. 12:482-487 (2002)). Although the etiology of DME is not fully understood, a primary cause of macular thickening appears to involve the diffusion of proteins and lipids across the retinal endothelium into the retina resulting in fluid retention and lipid exudates within the macula (Knudsen et al., Diabetes Care 25:2328-2334 (2002)). Over the past decade, a number of groups have demonstrated that growth factors and hormones, including vascular endothelial growth factor (VEGF), angiotensin II, and interleukin-6, are elevated in the vitreous of individuals with PDR and DME (Aiello et al., N. Engl. J. Med. 331:1480-1487 (1994); Funatsu et al., Opthalmology 110:1690-1696 (2003); Funatsu et al., Am. J. Opthalmol. 133:537-543 (2002); Simo et al., Diabetes Care 27:287-288 (2004); Simo et al., Clin. Sci. (Lond.) 104:223-230 (2003); Adamis et al., Am. J. Opthalmol. 118:445-450 (1994); Miller et al., Am. J. Pathol. 145:574-584 (1994)). The vitreous also contains anti-angiogenic and anti-permeability factors, such as pigment epithelium-derived factor (PEDF) and angiostatin, which can oppose the effects of VEGF (King et al., N. Engl. J. Med. 342:349-351 (2000); Ogata et al., Am. J. Opthalmol. 134:348-353 (2002); Raisler et al., Proc. Natl. Acad. Sci. U.S.A. 99:8909-8914 (2002); Dawson et al., Science 285:245-248 (1999); Spranger et al., Diabetologia 43:1404-1407 (2000)). These reports support the general proposition that vitreous fluid contains proteins that correlate with specific retinal pathologies, and that proteins in the vitreous compartment affect retinal vascular functions. A variety of retinal vascular conditions are believed to be associated with increased permeability; many of these conditions, e.g., the ischemic retinopathies, are thought to be mediated by these and other as yet unknown factors.

SUMMARY

The present invention is based, at least in part, on the identification of extracellular erythrocyte carbonic anhydrase-1 (CA-1) and carbonic anhydrase-2 (CA-2) as potent vascular permeability factors in retina and brain. Inhibition of this pathway underlying hemorrhage-induced blood vessel leakage provides new therapeutic opportunities in the treatment of retinal and cerebral edema. The proteins identified in the screens described herein are useful in novel therapeutic and diagnostic methods for treating disorders associated with excessive vascular permeability.

In one aspect, the invention provides methods for the treatment of disorders associated with excessive vascular permeability. The methods include administering to the subject a therapeutically effective amount of one or more of:

an inhibitor of Carbonic Anhydrase-1 (CA-1) and/or CA-2 signaling (e.g., an inhibitor of CA-1 and/or CA-2 itself, or an inhibitor that selectively targets extracellular CA-1 and/or CA-2, or an inhibitor of a downstream element in the CA-1/CA-2 signalling pathway that leads to increased vascular permeability (e.g., as illustrated in FIG. 6)), and optionally a second treatment that decreases vascular permeability, e.g., an inhibitor of Vascular Endothelial Growth Factor (VEGF) signalling (e.g., an inhibitor of VEGF itself or an inhibitor of a downstream element in the VEGF signalling pathway that leads to increased vascular permeability, as described herein);

an inhibitor of a kallikrein/kinin pathway, as described herein; and/or a Complement-1 Inhibitor (C1-INH) agonist, e.g., a C1-INH polypeptide, polynucleotide, or biologically active fragment thereof, or a small molecule, as described herein.

In some embodiments, the methods include the administration of an inhibitor of CA-2 signalling, in addition to or in place of an inhibitor of CA-1. In some embodiments, the methods include the administration of one or more inhibitors that inhibit both CA-1 and CA-2 isozymes. In some embodiments, the inhibitor is unable to cross the plasma membrane, so that an inhibitor applied extracellularly remains extracellular. In some embodiments, such inhibitors are hydrophilic, or include a hydrophilic moiety or other moiety that reduces or eliminates their ability to cross the plasma membrane.

In some embodiments, the inhibitor is isozyme specific, i.e., inhibits CA-1 and/or CA-2, but does not significantly inhibit other isozymes of CA.

In some embodiments, e.g., for the treatment of disorders associated with excessive retinal vascular permeability, both an inhibitor of CA-1 signaling and an inhibitor of VEGF signalling are administered, e.g., in a single composition.

The methods can include administering a composition described herein by local administration to the eye of the subject, e.g., by injection into the vitreous or aqueous humor of the eye, or by intrabulbar injection, or by administration as eye drops. In some embodiments, the methods include the use of a local drug delivery device (e.g., a pump or a biocompatible matrix) to deliver the composition. In other embodiments, the composition is delivered via injection into the cerebral fluid or cerebral spinal fluid. In some embodiments, the administration is systemic.

As used herein, disorders associated with excessive vascular permeability include, but are not limited to, disorders associated with increased retinal or cerebral vascular permeability and/or vasogenic edema. Described herein are methods of treating such disorders, e.g., by decreasing vascular permeability, e.g., decreasing retinal vascular permeability in the eye of a subject or decreasing cerebral vascular permeability in the brain of a subject. In some embodiments, the methods described include a step of selecting a subject on the basis that the subject has, or is at risk for developing, a disorder associated with excessive vascular permeability, as described herein.

Disorders associated with excessive vascular permeability and/or edema in the brain include, but are not limited to, cerebral edema, intracerebral hemorrhage, subdural hemorrhage, and hemorrhagic stroke. Cerebral edema is an increase in brain volume caused by an absolute increase in cerebral tissue fluid content; vasogenic cerebral edema arises from transvascular leakage caused by mechanical failure of the endothelial tight junctions of the blood-brain barrier (BBB).

Disorders associated with excessive vascular permeability and/or edema in the eye, e.g., in the retina or vitreous, include, but are not limited to, age-related macular degeneration (AMD), retinal edema, retinal hemorrhage, vitreous hemorrhage, macular edema (ME), diabetic macular edema (DME), proliferative diabetic retinopathy (PDR) and nonproliferative diabetic retinopathy (DR). Retinal edema is the accumulation of fluid in the intraretinal space. DME is the result of retinal microvascular changes that occur in patients with diabetes. This compromise of the blood-retinal barrier leads to the leakage of plasma constituents into the surrounding retina, resulting in retinal edema. Other disorders of the retina include retinal vein occlusions (e.g., branch or central vein occlusions); radiation retinopathy; sickle cell retinopathy; retinopathy of prematurity; Von Hipple Lindau disease; posterior uveitis; chronic retinal detachment; Irvine Gass Syndrome; Eals disease; retinitis; and/or choroiditis.

Other disorders associated with increased permeability include, but are not limited to, excessive vascular permeability associated with hypertension or inflammation; increased systemic vascular permeability, e.g., associated with septic shock, scurvy, anaphylaxis; and hereditary or acquired angioedema (both of which have been linked to C1 inhibitor deficiency). In some embodiments, the disorders associated with vascular permeability that are treated by a method described herein exclude hereditary or acquired angioedema.

In some embodiments, the disorder associated with increased permeability is also associated with hemorrhage, i.e., bleeding into the affected area. In some embodiments, the disorder associated with increased permeability is also associated with lysis of erythrocytes in the affected area.

In some embodiments, the disorder associated with increased permeability is also associated with an increased volume of fluid in the tissue, e.g., edema, and the methods described herein result in a reduction in the volume of fluid. Generally, the fluid is extracellular. Thus, included herein are methods for reducing the fluid volume in a tissue.

The invention also includes the pharmaceutical compositions described herein, e.g., compositions including an inhibitor of CA-1 and/or CA-2 signaling, and optionally an inhibitor of VEGF signalling, and a physiologically acceptable carrier. Further, the invention includes pharmaceutical compositions including a C1-INH polypeptide, polynucleotide, or biologically active fragment thereof, and a physiologically acceptable carrier. In some embodiments, the composition is adapted for injection into the vitreous or aqueous humor of a mammalian eye, or for use as eye drops. In some embodiments, the composition is adapted for intrathecal, e.g., subdural or subarachnoid, delivery.

In another embodiment, the invention includes pharmaceutical compositions including an inhibitor of a kallikrein/kinin pathway, and a physiologically acceptable carrier.

The methods described herein also include methods for diagnosing a subject with a disorder associated with excessive vascular permeability as described herein, by detecting a level of CA-1 and/or CA-2 in a sample from the subject, e.g., from the eye (e.g., the vitreous or aqueous humor) or the brain (e.g., cerebral fluid or cerebrospinal fluid (CSF)) of the subject and comparing the level to a reference, e.g., a control reference that represents the level of CA-1 and/or CA-2 in an unaffected subject. The presence of a level of CA-1 and/or CA-2 that is elevated, e.g., significantly elevated, as compared to the reference indicates that the subject has a disorder associated with excessive vascular permeability.

In another aspect, the invention includes methods for selecting a subject or population of subjects for participation in a clinical trial of a treatment for a disorder associated with excessive vascular permeability. The methods include detecting a level of CA-1 and/or CA-2 in a sample from the subject, e.g., from the eye (e.g., the vitreous or aqueous humor) or the brain (e.g., cerebral fluid or CSF) of the subject; comparing the level to a reference; and selecting the subject on the basis of the level of CA-1 and/or CA-2 as compared to the reference. For example, the subjects can be selected for or against if they have an elevated level of CA-1 and/or CA-2, or can be categorized depending on the level of CA-1 and/or CA-2.

The invention further provides methods for diagnosing subjects with a disorder associated with excessive vascular permeability by detecting a level of one or more, e.g., 2, 3, 4, 5, 7, 10, 12, 15, 20, 25, or 30, of the proteins, or mRNA encoding the protein(s), listed in Table 2 in a sample from the subject, e.g., from the eye (e.g., the vitreous or aqueous humor) or the brain (e.g., cerebral fluid or CSF) of the subject; and comparing the level of the protein or mRNA a reference. A significant difference in a level of the protein or mRNA as compared to the reference, e.g., an increase or decrease as shown in Table 2 for a disease state as compared to an unaffected individual, e.g., a significant increase in at least 2 proteins and/or a significant decrease in at least 2 proteins indicates that the subject has a disorder associated with excessive vascular permeability.

The invention further provides methods for identifying candidate compounds for the treatment of a disorder associated with excessive vascular permeability. The methods include providing a model of a disorder associated with excessive vascular permeability, e.g., a model of diabetic retinopathy/retinal vascular permeability or of hemorrhagic stroke; contacting the model with a test compound; detecting a level of one or more, e.g., 2, 3, 4, 5, 7, 10, 12, 15, 20, 25, or 30, of the proteins listed in Table 2, or mRNA encoding the protein(s); and comparing the level of the protein or mRNA a reference. A test compound that causes a significant difference in a level of the protein or mRNA as compared to the reference, e.g., an increase or decrease that is the inverse of the difference shown in Table 2 for a disease state as compared to an unaffected individual, is a candidate compound for the treatment of a disorder associated with excessive vascular permeability. In some embodiments, the methods include detecting the level of a protein or mRNA selected from the group consisting of one or more of acute-phase response proteins (alpha-1-antitrypsin, α-2-HS-glycoprotein, angiotensinogen, chitinase 3-like 1, orosomucoid-1 and -2) and proteins involved in cell growth, maintenance, and metabolism-(carbonic anhydrase 1, Glyceraldehyde 3 phosphate dehydrogenase, gelsolin isoform a, pigmented epithelium-derived factor, Dickkopf related protein-3); complement activation (complement C4B, complement component 9, clusterin isoform 1); and cell adhesion proteins (α-2-glycoprotein 1-zinc, galectin-3 binding protein).

The invention also relates to methods for predicting whether a subject has progressive retinopathy, i.e., is likely to progress in retinopathy severity. The methods include providing a sample from the subject, e.g., from the eye, e.g., the vitreous or aqueous humor, of the subject; detecting a level of one or more, e.g., 2, 3, 4, 5, 7, 10, 12, 15, 20, 25, or 30, of the proteins listed in Table 2, or mRNA encoding the protein(s), in the sample; and comparing the level of the protein or mRNA a reference. A significant difference in a level of the protein or mRNA as compared to the reference, e.g., an increase or decrease as shown in Table 2 for a disease state as compared to an unaffected individual, indicates that the subject has progressive retinopathy.

Significant differences in the level of a level of one or more, e.g., 2, 3, 4, 5, 7, 10, 12, 15, 20, 25, or 30, of the proteins listed in Table 2 or mRNA encoding the protein(s), as compared to the level of the protein or mRNA in a reference are indicative of a subject's risk for development of a sight-threatening complication of retinopathy, e.g., ME, PDR, DME.

The invention also includes methods for evaluating a treatment for a disorder associated with excessive vascular permeability. The methods include detecting a level of one or more, e.g., 2, 3, 4, 5, 7, 10, 12, 15, 20, 25, or 30, of the proteins listed in Table 2, or mRNA encoding the protein(s), in a sample from a subject, e.g., from the eye, e.g., the vitreous or aqueous humor, of the subject; administering one or more doses of a treatment to the subject, and comparing the level of the protein or mRNA to a reference, e.g., a level of the protein or mRNA prior to administration of the treatment. A significant difference in a level of the protein, e.g., an increase or decrease as shown in Table 2 for a disease state as compared to an unaffected individual, as compared to the reference indicates the efficacy of the treatment.

The invention also includes methods for determining when a treatment modality (e.g., administration of a compound as described herein, or another method of treating a disorder associated with excessive vascular permeability, as known in the art) that is administered to a subject to treat or prevent a disorder associated with excessive vascular permeability can be stopped. The methods include providing a sample from the subject, e.g., from the eye (e.g., the vitreous or aqueous humor) or the brain (e.g., cerebral fluid or cerebrospinal fluid (CSF)) of the subject; detecting a level of one or more, e.g., 2, 3, 4, 5, 7, 10, 12, 15, 20, 25, or 30, of the proteins listed in Table 2, or mRNA encoding the protein(s), in the sample; comparing the level of the protein or mRNA to a reference, e.g., a level of the protein or mRNA in an unaffected subject. A level of the protein or mRNA that approaches (e.g., is not significantly different from) the level of the protein or mRNA in a normal subject indicates that the treatment can be stopped.

Further, the invention includes methods for determining when a treatment for a disorder associated with excessive vascular permeability should be initiated in a subject. The methods include providing a sample from the subject, e.g., from the eye, e.g., the vitreous or aqueous humor, of the subject; detecting a level of one or more, e.g., 2, 3, 4, 5, 7, 10, 12, 15, 20, 25, or 30, of the proteins listed in Table 2, or mRNA encoding the protein(s), in the sample; and comparing the level of the protein or mRNA a reference. A significant difference in a level of the protein or mRNA, e.g., an increase or decrease as shown in Table 2, and/or in FIG. 4 for a disease state as compared to an unaffected individual, as compared to the reference indicates that the treatment should be initiated.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-F are bar graphs illustrating the effects of carbonic anhydrase-1 (CA-1) on focal microvascular leakage in the vitreous, measured by vitreous fluorophotometry. Effects of CA-1, CA-2, and acetazolamide on retinal vascular permeability (RVP) (3A). Time course of RVP following a single intravitreal injection of CA-1 (3B). Effects of CA-1, VEGF, C1-INH, and AGT on vitreous fluorescein intensity (3C). Inhibition of the CA-1-stimulated increase in vitreous fluorescein intensity by Hoe 140 and desHoe 140 (3D). Effect of leupeptin and aprotinin on CA-1 stimulated vitreous fluorescein (3E). Effect of transplant of human vitreous, with or without pretreatment with acetazolamide, into rat vitreous followed by measurement of RVP using vitreous fluorophotometry (3F). Significant changes are indicated by *P<0.05 and **P<0.01 vs BSS, κP<0.05 vs VEGF, ΨP<0.05 vs CA-1, and ΦP=0.017 vs PDR with acetazolamide.

FIGS. 4A-4C are a table listing the results of proteomic analysis performed on 50 µl of undiluted vitreous from NDM (n=5) and diabetic patients with noDR (n=4) and PDR (n=3). Protein matches for the 12 vitreous samples were compiled, and the numbers of unique peptides (median and mean ±SD) for each protein from the 3 groups of subject are shown.

1: Indicates protein is significantly correlated with carbonic anhydrase I according to Spearman correlations.

2: Indicates protein is significantly correlated with carbonic anhydrase II according to Spearman correlations.

Differences among the three groups were tested using the nonparametric test, Kruskal-Wallis analysis of ranks. If the test statistic from this analysis was significant, differences between group pairs were then examined using the nonparametric test, Wilcoxon two-sample test. For these tests:

a: Refers to significant differences between NDM group and DM group b: Refers to significant differences between DM group and PDR group c: Refers to significant differences between NDM group and PDR group Test statistics with P values of less than or equal to 0.05 are shown in gray, and bolded. Test statistics with P values of greater than 0.05 are not highlighted in this table.

FIG. 5A-I are a series of photographs illustrating blood-brain barrier permeability to Evan's blue dye in rat. Photography of the posterior (a, d, g), anterior surfaces (b, e, h), and 3× magnification of posterior focal lesions (c, f, i) of the rat brain 24 hours after subdural space injection (indicated by arrows) of 50 µL BSS vehicle (a-c), 1 µg/50 µL CA-1 (d-f), and 2.5 µl lysed RBC/20 µL BSS (g-i).

FIG. 5J is a bar graph of levels of Evan's Blue dye extracted and quantified from the brain surface 24 hours after subdural space injection of 50 µL BSS vehicle, 1 µg/50 µL CA-1 or 10 µg/50 µL bovine serum albumin (BSA) or C1-inhibitor (C1-INH). Data represent means ±SD. n=4-5. Significant changes are indicated by * P<0.05 vs BSS and Ψ P<0.05 vs 1 µg CA-1.

Figure 6:
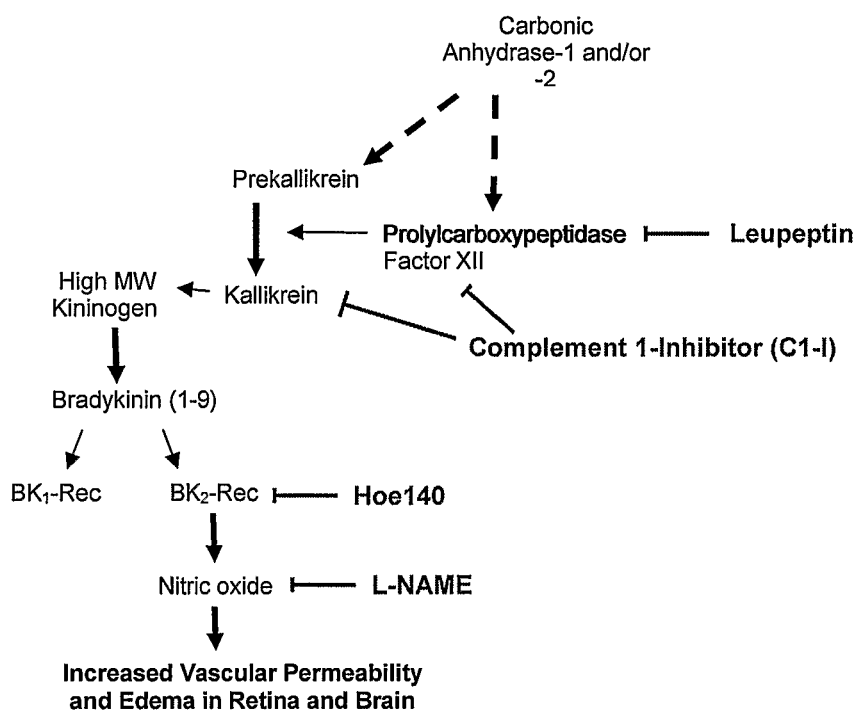

FIG. 6 is a hypothetical model of carbonic anhydrase-induced permeability. Dashed arrows indicate the possible presence of one or more unknown intermediaries; solid arrows represent what is believed to be a direct connection.

DETAILED DESCRIPTION

Functional proteomics was used to identify novel factor(s) that contribute to the changes observed in the eye associated with diabetes. Such changes include the progression of non-proliferative retinopathy, the onset of proliferative diabetic retinopathy (PDR), and the excessive increase in retinal vascular permeability (RVP) that is observed in proliferative diabetic retinopathy (PDR), as well as at other stages of a retinopathy, e.g., in the case of diabetic macular edema. The effect of diabetic retinopathy on the vitreous proteome was characterized by using mass spectrometry to inventory and compare the vitreous protein composition of nondiabetic subjects and diabetic patients with or without active PDR and macular edema. The effects of vitreous proteins on RVP were assessed by intravitreal injection in rats.

As described herein, these studies identified a number of proteins whose expression levels are altered in PDR and/or macular edema. Among those proteins are carbonic anhydrase-1 (CA-1) and carbonic anhydrase-2 (CA-2). Carbonic anhydrase (CA) includes a family of at least 12 active isoenzymes that catalyzes the hydration of carbon dioxide to bicarbonate. These isoenzymes differ in their tissue distribution, subcellular localization, and $IC_{50}$ to clinical CA inhibitors. Intracellular CA-2 and CA-4 isoenzymes, which are expressed in the retinal pigmented epithelium and corneal vascular endothelium, regulate intraocular pressure by facilitating ion and water transport across ocular barriers (Srinivas et al., Invest. Opthalmol. Vis. Sci. 43, 3273-3278 (2002); Wolfensberger et al., Invest. Opthalmol. Vis. Sci. 35, 3401-3407 (1994)). Production of carbonate by carbonic anhydrase 9 (CA-9), a membrane bound isoenzyme, has been implicated in tumor acidification and angiogenesis (Giatromanolaki et al., Cancer Res. 61, 7992-7998 (2001)).

While these effects of cellular CA are well documented, the physiological effects of soluble extracellular CA in the vitreous fluid are unknown. Pharmacological effects of CA inhibitors on glaucoma and macular edema have been previously attributed to the inhibition of CA-2 and CA-4 isoenzymes and bicarbonate-coupled active ion transport (Srinivas et al., (2002), supra; Wolfensberger et al., (1994), supra; see also Wolfensberger, Doc. Opthalmol. 97:387-397 (1999)). Although a molecular connection between increased CA levels and diabetic retinopathy had not been previously identified, a single small pilot study has suggested that acetazolamide may have beneficial effects on fluorescein-angiographic findings and perimetric data in patients with DME (Giusti et al., Int. Opthalmol. 24, 79-88 (2001)).

The present study shows that both CA-1 and CA-2 are elevated in the vitreous of patients with PDR. While CA-2 and CA-4 are inhibited by acetazolamide and dorzolamide at low nM concentrations, the Ki of these inhibitors for CA-1 is 250 nM and 50 µM, respectively (Weber et al., J. Med. Chem. 47:550-557 (2004)). Since the Ki of CA inhibitors for CA-1 differ by 2 to 3 orders of magnitude, selection of inhibitors with efficacy against CA-1 and drug delivery to the vitreous are important considerations for patients with DR. In addition, a recent report has shown that arylsulfonamide-type cyclooxygenase COX-2-selective inhibitors, including Celecoxib, also inhibit CA-2 at low nanomolar concentrations (Weber et al., (2004) supra). Since this class of drugs is currently being investigated as a treatment for DR, the cross-reactivity to CA-2 could contribute to the efficacy and complications associated with this therapeutic approach.

CA-1 is demonstrated herein to be a novel activator of the contact/kallikrein system that increases RVP and contributes to the RVP in subjects with DME and PDR. As described herein, CA-1 acts through a complement 1 inhibitor (C1-INH)-sensitive protease pathway that is independent of VEGF. To investigate the broad relevance of extracellular CA-1 in vasogenic edema, the effect of CA-1 on blood brain barrier permeability was examined. Infusion of CA-1 into the subdural space in rats induced both diffuse and focal lesions of increased cerebral vascular permeability.

As one example, high levels of carbonic anhydrase-1 (CA-1) were identified in vitreous from patients with advanced diabetic retinopathy. As described herein, intravitreal injection of CA-1 in rats increased retinal vascular permeability. This response was comparable in magnitude, additive to vascular endothelial growth factor-induced permeability, and blocked by complement 1 inhibitor (C1-INH) and antagonists of the kalhkrein-bradykinin receptor pathway. Further, carbonic anhydrase inhibition by acetazolamide blocked the increased retinal permeability in rats induced by transplant of vitreous from patients with advanced diabetic retinopathy. Therefore, carbonic anhydrase is a novel physiological activator of the contact/kallikrein system via a C1-INH-sensitive protease pathway, and plays a major role in the retinal vascular permeability in diabetic retinopathy. The kallikrein pathway is a novel target for diagnostic and therapeutic interventions in excessive vascular permeability.

In addition, it was discovered that, surprisingly, the effects of carbonic anhydrase are additive to the effects of VEGF. Thus, the invention includes compositions including a combination of an inhibitor of carbonic anhydrase/kallikrein signalling, plus an inhibitor of VEGF signalling, and methods of treatment using those compositions.

Furthermore, the data presented herein shows that extracellular CA-1 inside either the blood-retinal barrier or blood-brain barrier induces vasogenic edema. As one theory, not meant to be limiting, the release of erythrocyte-derived CA-1 could account for the increased vascular permeability and edema in diabetic retinopathy or following subdural hematoma. Thus, delivery of CA-1 and/or CA-2 selective inhibitors, C1-INH, and/or antagonists of the kallikrein-kinin system may provide novel therapeutic opportunities for the treatment of neurovascular edema associated with conditions such as PDR, ME, DME, age-related macular degeneration, subdural hemorrhage, and hemorrhagic stroke.

Pharmaceutical Compositions and Methods of Administration

Described herein are pharmaceutical compositions that can include as active agents one or more of an inhibitor of CA-1 and/or CA-2 signaling; an inhibitor of kallikrein/kinin signaling; and a C1-INH agonist, e.g., a C1-INH polypeptide, polynucleotide, active fragments thereof, and small molecules. The methods described herein include the manufacture and use of such pharmaceutical compositions.

FIG. 6 is a hypothetical model of carbonic anhydrase-induced permeability, illustrating the pathways that can be targeted using methods described herein. Dashed arrows indicate the possible presence of one or more unknown intermediaries; solid arrows represent what is believed to be a direct connection.

In some embodiments, the invention includes a pharmaceutical composition that includes an inhibitor of kallikrein/kinin signaling. As shown in FIG. 6, the kallikrein/kinin signalling system includes kallikrein (KK), and high molecular weight kininogens (HK); see, e.g., Mahabeer and Bhoola, Pharmacol. Ther. 88(1):77-89 (2000); Campbell, Clin. Exp. Pharmacol. Physiol. 28(12):1060-5 (2001); and Bhoola et al., Pharm. Rev. 44:1-80 (1992). Kallikrein enzymes are a group of serine proteases found in many different tissues and body fluids. Activation of kallikrein results in cleavage of kininogen, which liberates bradykinin (BK), among other vasoactive peptides. See, e.g., Campbell et al., Braz. J. Med. Biol. Res. 33(6):665-77 (2000). Components of the system have been described in the eye, see, e.g., Igic, Exp. Eye Res. 41(1):117-20 (1985); Gao, Diabetologia. 46(5):689-98 (2003), Epub 5.13.03; Ma et al., Exp. Eye Res. 63(1):19-26 (1996); and Wilkinson-Berka and Fletcher, Curr Pharm Des. 10(27):3313-30 (2004).

The serine protease prolylcarboxypeptidase (PRCP) is a major cell surface prekallikrein activating enzyme; Shariat-Madar et al., Blood 103:4554-4561 (2004), and anti-PRCP antibodies have been shown to block activation of kallikrein; Shariat-Madar et al., Am. J. Physiol. Heart Circ. Physiol. Epub ahead of print, Aug. 19, 2005 (doi:10.1152/ajpheart.00715.2005). A number of PRCP inhibitors are known in the art, e.g., leupeptin, angiotensin II, bradykinin, anti-PRCP, diisopropyl-fluorophosphonate (DFP), phenylmethylsulfonyl fluoride (PMSF), Z-Pro-Proaldehyde-dimethyl acetate, and other small molecules; see, e.g., Shariat-Madar et al., (2004), supra; and Shariat-Madar et al., J Biol. Chem. 277:17962-17969 (2002).

Suitable kallikrein/kinin signalling inhibitors can act at any point in the kallikrein/kinin pathway, and include, but are not limited to, inhibitory nucleic acids, e.g., antisense, RNAi, and aptamers, that are specific for a protein in the pathway; and BK2 and BK1 receptor antagonists, e.g., Hoe 140 and desHoe140 (Han et al., J. Clin. Invest. 109(8): 1057-63 (2002)), see also Howl and Payne, Expert Opin Ther Targets. 7(2):277-85 (2003); kininase I and kininase II (angiotensin-converting enzyme); Kallistatin (Zhou et al., J. Biol. Chem. 267(36):25873-80 (1992)), Kallikrein-binding protein (e.g., as described in Gao et al, Diabetologia 46:689-698 (2003)) or Kunitz domain Kallikrein inhibitors, e.g., as described in U.S. Pat. No. 5,780,265, e.g., DX-88 (SEQ ID NO:1; Dyax, Cambridge, MA), described in Markland et al., Biochemistry 35:8058- 8067 (1996), and one or more of U.S. Pat. Nos. 6,423,498, 6,333,402, 6,103,499, 6,071,723, 6,057,287, 6,010,880, 5,994,125, 5,837,500, 5,795,865, and 5,663,143. In some embodiments, the kallikrein/kinin inhibitor is an anti-prekallikrein antibody or antigen-binding fragment thereof, that can block the CA-1 response by blocking the activation of prekallikrein to kallikrein, e.g., by interfering with access of prekallikrein activating proteases, such as Factor XII.

In some embodiments, the active ingredient is a Complement-1 Inhibitor (C1-INH; GeneID: 710; UniGene Hs.384598) agonist, e.g., C1-INH polynucleotide (e.g., *Homo Sapiens*: GenBank No. S76944.2), polypeptide (e.g., *Homo Sapiens*: GenBank No. AAB33044.2), or a biologically active mutant or fragment thereof, e.g., as described in Reboul et al., Biochem. J. 244(1):117-21 (1987); Lamark et al., Protein Expr Purif. 22(2):349-58 (2001); and/or Bos et al., J. Biol. Chem. 278(32):29463-70 (2003), Epub 5.27.03, and Zahedi et al., J. Immunol. 167:1500-1506 (2001). A biologically active fragment or mutant of C1-INH retains the ability to significantly inhibit the serum protease kallikrein. Methods for making and testing such fragments and mutants are known in the art.

In some embodiments, the active ingredient is an inhibitor of CA-1 and/or CA-2 signalling. Inhibitors of CA-1 and/or CA-2 signalling include CA-1 and/or CA-2 inhibitors that act directly on CA-1 and/or CA-2, e.g., small molecule inhibitors. Examples include small molecule inhibitors such as certain sulfonamides and sulfamides, e.g., N-unsubstituted sulfonamides, e.g., acetazolamide, methazolamide, or 3-acetoxymercuri-4-aminobenzenesulfonamide (Chakravarty and Kannan, J Mol. Biol. 243(2):298-309 (1994)), benzolamide (Casini et al., Bioorg Med Chem. Lett. 13(17):2867-73 (2003)), 4-sulfamoylphenylthioureas (Innocenti et al., J Med. Chem. 47(21):5224-9 (2004)); E7070 (Abbate et al., Bioorg Med Chem. Lett. 14(1):217-23 (2004)); aliphatic sulfainates (Winum et al., J Med. Chem. 46(25):5471-7 (2003)); and arylsulfonamide-type COX-2 inhibitors (Weber et al, J Med. Chem. 47(3):550-7 (2004)). A number of other CA 1 and/or CA 2 inhibitors, and methods for developing and evaluating novel inhibitors, are known in the art, see, e.g., Supuran et al., Med. Res. Rev. 23(2):146-189 (2003); Supuran et al., Bioorg Med Chem. Lett. 11(4):575-82 (2001); and Cecchi et al., Bioorganic & Medicinal Chemistry Letters 14:5775-5780 (2004).

In some embodiments, the inhibitor is selective for the CA-1 and/or CA-2 isozymes, e.g., does not substantially inhibit the other isozymes of CA. In some embodiments, the inhibitor acts on CA-1 and/or CA-2 with an affinity in the low nanomolar range, e.g., IC50≤100 nM, but has an IC50 for the other isozymes of CA that is an order of magnitude higher. In some embodiments, the inhibitor has an IC50 for CA-1 and/or CA-2 of less than about 50 nM, e.g., less than about 20 nM. Methods for evaluating the IC50 of a given inhibitor are known in the art, see, e.g., Supuran et al., (2003), supra; Cecchi et al., (2004), supra. In some embodiments, the inhibitor of CA-1 and/or CA-2 is sufficiently hydrophilic that it does not enter erythrocytes and therefore does not act on CA-1 or CA-2 inside intact erythrocytes. In a preferred embodiment, the inhibitor is selective for CA-1.

In some embodiments, the composition includes at least two active ingredients, e.g., an inhibitor of CA-1 and/or CA-2 signalling and an inhibitor of Vascular Endothelial Growth Factor (VEGF) signalling.

In some embodiments, the composition further includes an inhibitor of VEGF signalling. A number of inhibitors of VEGF signalling are known in the art and can include, e.g., ZD6474 (Tuccillo et al., Clin Cancer Res. 11 (3):1268-76 (2005)); COX-2, Tie2 receptor, angiopoietin, and neuropilin inhibitors; pigment epithelium-derived factor (PEDF), endostatin, and angiostatin (King et al., N. Engl. J. Med. 342:349-351 (2000); Ogata et al., Am. J. Opthalmol. 134: 348-353 (2002); Raisler et al., Proc. Natl. Acad. Sci. U.S.A. 99:8909-8914 (2002); Dawson et al., Science 285:245-248 (1999); Spranger et al., Diabetologia 43:1404-1407 (2000)); VEGF inhibitory aptamers, e.g., Macugen™ (pegaptanib, Pfizer); antibodies or fragments thereof, e.g., anti-VEGF antibodies, e.g., bevacizumab (Avastin™, Genentech), or fragments thereof, e.g., ranibizumab (Lucentis™, Genentech); soluble fms-like tyrosine kinase 1 (sFlt1) polypeptides or polynucleotides (Harris et al., Clin Cancer Res. 7(7):1992-7 (2001); U.S. Pat. No. 5,861,484); PTK787/ZK222 584 (Maier et al., Graefes Arch Clin Exp Opthalmol. 243(6):593-600 (2005); KRN633 (Maier et al., Mol Cancer Ther. 3(12): 1639-49 (2004)); VEGF-Trap™ (Regeneron); intravitreal steroids, e.g., triamcinolone; and Alpha2-antiplasmin (Matsuno et al, Blood 120:3621-3628 (2003)). For reviews of VEGF and its inhibitors, see, e.g., Campochiaro, Expert Opin Biol Ther. 4(9):1395-402 (2004); Ferrara, Endocr. Rev., 25(4):581-611 (2004); and Verheul and Pinedo, Drugs Today (Barc). 39 Suppl C:81-93 (2003).

In some embodiments, inhibitory nucleic acid molecules that are targeted to a selected target RNA, e.g., antisense, siRNA, ribozymes, and aptamers, are used. In some embodiments, the inhibitory nucleic acid targets an mRNA encoding a protein listed in Table 2, and/or in FIG. 4 that is increased in a disease state as compared to an unaffected individual. In some embodiments, the inhibitory nucleic acid targets a protein in the CA-1/CA-2 signalling pathway.

siRNA Molecules

RNAi is a process whereby double-stranded RNA (dsRNA, also referred to herein as si RNAs or ds siRNAs, for double-stranded small interfering RNAs,) induces the sequence-specific degradation of homologous mRNA in animals and plant cells (Hutvagner and Zamore, Curr. Opin. Genet. Dev. 12:225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell. 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque 418(6896):435-8 (2002), Epub 1.26.02).

Antisense

An "antisense" nucleic acid can include a nucleotide sequence that is complementary to a "sense" nucleic acid encoding a protein, e.g., complementary to the coding strand of a double-stranded cDNA molecule or complementary to a TEF mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim, Biophys. Acta. 1489:141-58 (1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des. 6:569-84 (1991); Helene, Ann. N.Y. Acad. Sci. 660:27-36 (1992); and Maher, Bioassays 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993).

Formulation of Pharmaceutical Compositions

Pharmaceutical compositions typically include the active ingredient and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is typically formulated to be compatible with its intended route of administration. Examples of routes of administration include parenteral, e.g., intravenous, intradermal, subcutaneous, oral (e.g., inhalation), intrathecal (e.g., subdural or subarachnoid), transdermal (topical), transmucosal, and rectal administration. In some embodiments, e.g., for treating disorders associated with excessive retinal vascular permeability, the composition is administered directly to the eye, e.g., by eye drops, or directly into the eye across the blood-retinal barrier, e.g., by implants, peribulbar injection, or intravitreous injection. In some embodiments, e.g., for treating disorders associated with excessive cerebral vascular permeability, the composition is delivered across the blood-brain barrier, e.g., intrathecal, e.g., subdural or subarachnoid delivery, e.g., delivery into the cerebral or cerebrospinal fluid. In some embodiments, e.g., for administration to the vitreous or retina, the active ingredient is incorporated into a polymer matrix that is implanted into or near the site of intended delivery.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In some embodiments, the composition is especially adapted for administration into or around the eye. For example, a composition can be adapted to be used as eye drops, or injected into the eye, e.g., using peribulbar or intravitreal injection. Such compositions should be sterile and substantially endotoxin-free, and within an acceptable range of pH. Certain preservatives are thought not to be good for the eye, so that in some embodiments a non-preserved formulation is used. Formulation of eye medications is known in the art, see, e.g., *Ocular Therapeutics and Drug Delivery: A Multi-Disciplinary Approach*, Reddy, Ed. (CRC Press 1995); Kaur and Kanwar, Drug Dev Ind Pharm. 2002 May; 28(5): 473-93; *Clinical Ocular Pharmacology*, Bartlett et al. (Butterworth-Heinemann; 4th edition (Mar. 15, 2001)); and *Ophthalmic Drug Delivery Systems* (*Drugs and the Pharmaceutical Sciences: a Series of Textbooks and Monographs*), Mitra (Marcel Dekker; 2nd Rev&Ex edition (Mar. 1, 2003)).

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Administration of a therapeutic compound described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Compositions including nucleic acid compounds can be administered by any method suitable for administration of nucleic acid agents. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996). In some embodiments, the nucleic acid compounds comprise naked DNA, and are administered directly, e.g., as described herein. The inhibitory nucleic acid molecules described herein can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid nucleic acid molecules to peptides or antibodies that bind to cell surface receptors or antigens. The inhibitory nucleic acid nucleic acid molecules can also be delivered to cells using the vectors described herein. To achieve sufficient intracellular concentrations of the inhibitory nucleic acid molecules, vector constructs in which the inhibitory nucleic acid nucleic acid molecule is placed under the control of a strong promoter can be used.

In some embodiments, the compositions are prepared with carriers that will protect the active ingredient against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially, e.g., from Alza Corporation or Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The delivery systems can include time-release, delayed release or sustained release delivery systems. Such systems can avoid repeated administrations of the agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109.

Delivery systems can also include non-polymer systems, e.g., lipids including sterols such as cholesterol, cholesterol esters and fatty acids or neutral fats such as mono-, di- and tri-glycerides; hydrogel release systems; sylastic systems; peptide based systems; wax coatings; compressed tablets using conventional binders and excipients; partially fused implants; and the like. Specific examples include, but are not limited to erosional systems in which the active agent is contained in a form within a matrix such as those described in U.S. Pat. Nos. 4,452,775, 4,667,014, 4,748,034 and 5,239,660, and diffusional systems in which an active component permeates at a controlled rate from a polymer such as described in U.S. Pat. Nos. 3,832,253, and 3,854,480. Pump-based hardware delivery systems can be used, some of which are adapted for implantation. In addition, U.S. Pat. No. 6,331,313 describes a biocompatible ocular drug delivery implant device that can be used to deliver active agents directly to the macular region.

Use of a long-term sustained release implant may be particularly suitable for treatment of chronic conditions. Long-term release means that the implant is constructed and arranged to delivery therapeutic levels of the active ingredient for at least 30 days, e.g., 60 days. Long-term sustained release implants are known to those in the art and include some of the release systems described herein.

The pharmaceutical compositions can be included in a container, pack, or dispenser together with instructions for administration.

Methods of Treatment

The pharmaceutical compositions described herein are useful in the treatment of disorders associated with increased vascular permeability, as described herein.

As used in this context, to "treat" means to ameliorate at least one symptom of the disorder associated with increased vascular permeability. Often, increased systemic vascular permeability results in capillary leak syndrome and hypovolaemia; thus, a treatment can result in a reduction in capillary leakage and a return or approach to normovolemia. Administration of a therapeutically effective amount of a composition described herein for the treatment of a condition associated with increased vascular permeability will result in decreased vascular permeability. In diabetic retinopathy, administration of a therapeutically effective amount of a composition described herein may result in unobstructed vision, improved vision or reduction in the rate of visual loss.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in a method described herein, the therapeutically effective dose can be estimated initially from animal studies, e.g., from intravitreal injection in animals. A dose may be formulated in animal models to achieve a circulating plasma concentration range that includes the IC50 (i.e., the concentration of the test compound which achieves a half-maximal inhibition of symptoms) as determined in intravitreal injection. Such information can be used to more accurately determine useful doses in humans. Levels in plasma or vitreous may be measured, for example, by high performance liquid chromatography and mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the compositions described herein can include a single treatment or a series of treatments.

Methods of Diagnosis

Also described herein are methods for diagnosing a disorder associated with excessive vascular permeability as described herein, e.g., a disorder associated with excessive retinal vascular permeability. The methods include obtaining a sample from a subject, and evaluating the presence and/or level of one, two, three, four, five, six, seven, eight or more of the proteins listed in Table 2 or FIG. 4 in the sample, and comparing the presence and/or level with one or more references, e.g., a control reference that represents a normal level of the proteins, and/or a disease reference that represents a level of the proteins associated with diabetic retinopathy. Suitable reference values can include those shown in Table 2 or FIG. 4. The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. *Modern Genetic Analysis*, 1999, W. H. Freeman and Company; Ekins and Chu, Trends in Biotechnology, 1999, 17:217-218; MacBeath and Schreiber, Science 2000, 289(5485): 1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of two, three, four, five or more of the proteins listed in Table 2 or FIG. 4. In some embodiments, the proteins include acute-phase response proteins (alpha-1-antitrypsin, alpha-2-HS-glycoprotein, angiotensinogen, chitinase 3-like 1, orosomucoid-1 and -2); complement activation proteins (complement C4B, complement component 9, clusterin isoform 1); and cell adhesion proteins (alpha-2-glycoprotein 1-zinc, Galectin-3 binding protein).

In some embodiments, the presence and/or level of one or more of the proteins evaluated is comparable to the presence and/or level of the protein(s) in the disease reference, and the subject has one or more symptoms associated with diabetic retinopathy, then the subject has diabetic retinopathy. In some embodiments, the subject has no overt signs or symptoms of diabetic retinopathy, but the presence and/or level of one or more of the proteins evaluated is comparable to the presence and/or level of the protein(s) in the disease reference, then the subject has an increased risk of developing diabetic retinopathy. In some embodiments, the sample includes vitreous fluid; in other embodiments, the sample includes aqueous fluid. In some embodiments, once it has been determined that a person has diabetic retinopathy, or has an increased risk of developing diabetic retinopathy, then a treatment as described herein can be administered.

Methods of Screening

The invention includes methods for screening test compounds, e.g., polypeptides, peptides, polynucleotides, inorganic or organic large or small molecule test compounds, to identify agents useful in the treatment of opthalmological disorders associated with increased retinal vascular permeability, e.g., diabetic retinopathy.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity, Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the small organic molecules and libraries thereof can be obtained by systematically altering the structure of a first small molecule, e.g., a first small molecule that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to modulate expression of one or more of the proteins listed in Table 2, and/or in FIG. 4, decrease carbonic anhydrase-1 activity, or inhibit signalling via the kallikrein/kinin pathway can be evaluated. In the eye, for example, the ability of the test compounds to modulate expression of one or more of the proteins listed in 2, decrease carbonic anhydrase-1 activity, or modulate signalling via the kallikrein/kinin pathway, or affect vascular permeability, can be evaluated.

To identify inhibitors of CA (e.g., CA-1 or -2), the test sample can include a chromogenic substrate, which allows the detection of the esterase activity of the enzyme. In general, the assay will be carried out in a liquid sample, in the presence of purified CA polypeptide, the test sample, and a chromogenic substrate. For example, hydrolysis of p-nitrophenylacetate (e.g., available from Sigma-Adrich Corp., St. Louis, Mo., Cat. No. N-8130) can be evaluated, see, e.g., Pocker and Stone, Biochemistry, 7, 3021-3031 (1968); Lauwereys et al., EMBO J. 17(13):3512-3520 (1998)). In some embodiments, the assay is carried out in the presence of a plurality of isozymes, to determine whether the inhibitor is isozyme selective, i.e., inhibits one or more selected isozymes, e.g., CA-1 and/or CA-2, but does not substantially inhibit one or more other isozymes of CA. In some embodiments, the specific inhibitor inhibits one isozyme with an affinity in the low nanomolar range, e.g., IC50≤100 nM, but has an IC50 for other isozymes that is an order of magnitude higher. See, e.g., Supuran et al., Med. Res. Rev. 23(2):146-189 (2003); Supuran and Scozzafava, Exp. Opin. Ther. Patents 10:575-600 (2000); and Cecchi et al., Bioorganic & Medicinal Chemistry Letters 14:5775-5780 (2004).

In some embodiments, the test sample is an "engineered" in vivo model. For example, vitreous from a human subject, e.g., a human subject having diabetic retinopathy, can be transplanted into one or both eyes of an animal model, e.g., a rodent such as a rat. For example, about 10 µl of human vitreous can be injected into the rat vitreous compartment and the response on retinal vascular permeability measured. Alternatively or in addition, purified CA-1 and/or CA-2 can be injected. In some embodiments, the model animal also has diabetes, e.g., a streptozotocin-induced or genetic animal model of diabetes. In some experiments, the CA or human vitreous will be co-injected with other agents, e.g., test compounds, such as known or potential carbonic anhydrase inhibitors.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on two, three, four, five or more of the proteins listed in Table 2, and/or in FIG. 4. Ability to modulate signaling via the kallikrein/kinin pathway can be evaluated, e.g., using liberation of bradykinin or other proteolytic products of kininogen (see, e.g., Campbell et al., Braz J Med Biol Res. 2000 June; 33(6):665-77), and using the measurement of cyclic guanine monophosphate (cGMP). Vascular permeability can be evaluated, e.g., as described herein.

Figure 4A:
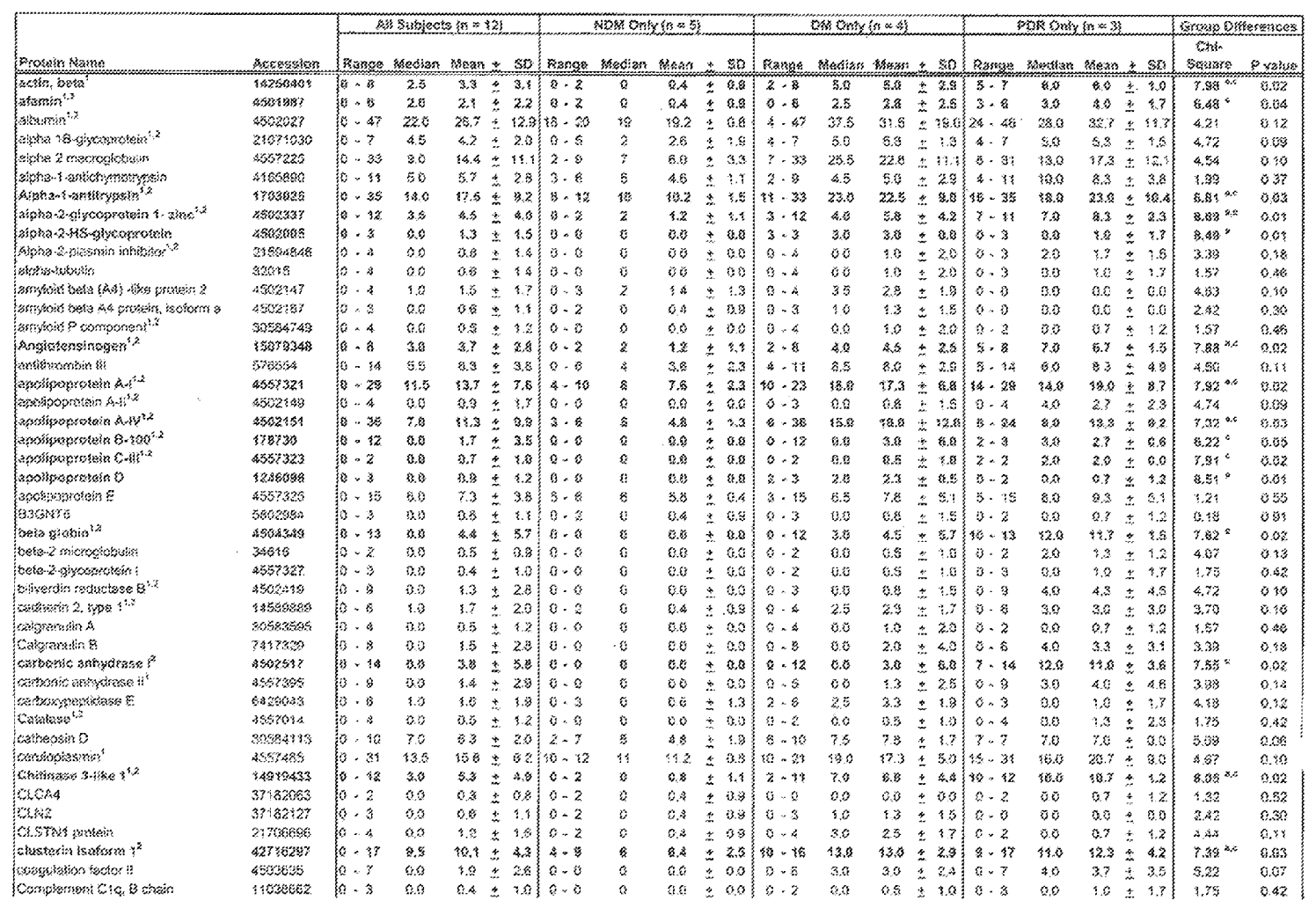

Test compounds identified as "hits" (e.g., test compounds that decrease vascular permeability, modulate levels of one or more proteins listed in Table 2, and/or in FIG. 4, decrease carbonic anhydrase-1 activity, or inhibit signalling via the kallikrein/kinin pathway) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating opthalmological disorders associated with increased retinal vascular permeability, as described herein, e.g., diabetic retinopathy. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of an opthalmological disorder associated with increased vascular permeability, as described herein. The animal can be monitored for a change in the disorder, e.g., for an improvement in a parameter of the disorder, e.g., a parameter related to clinical outcome. In some embodiments, the parameter is vascular permeability, and an improvement would be a decrease in vascular permeability. In some embodiments, the subject is a human, e.g., a human with diabetes, and the parameter is visual acuity.

The invention is further described in the following examples, which do not limit the scope of the invention described in the claims.

EXAMPLES

Example 1

Protein Inventory of Human Vitreous

To catalog the proteins present in human vitreous, proteomic analysis was performed.

Vitreous fluid was obtained from patients undergoing pars plana vitrectomy at the Beth Israel Deaconess Medical Center (Boston, Mass.) and Santa Barbara Cottage Hospital Eye Center (Santa Barbara, Calif.) in accordance with institutional review boards at both institutions. The reasons from vitrectomy included macular hole, epiretinal membrane, glaucoma, and retinal detachment. Samples were stored at −80° C. until used.

Vitreous samples were obtained from pars plana vitrectomy of non-diabetic mellitus (NDM) subjects (n=9), patients with diabetes mellitus and no diabetic retinopathy (noDR, n=4), and diabetic patients with PDR+/−DME (PDR, n=12). The study subject demographics are summarized in Table 1. This study included 25 subjects, including 7 females and 18 males. The PDR group subjects were younger ($P<0.05$) than the NDM and noDR groups. Eight subjects in the PDR group were diagnosed with diabetic macular edema.

TABLE 1

Demographics of Study Subjects.

| Group and Level of Retinopathy | n | Age years (mean ± SD) | Gender (F/M) | DM (type 1/2) | Duration (mean ± SD) | DME (y/n) |
|---|---|---|---|---|---|---|
| NDM | 8 | 72.4 ± 7.8 | 3/5 | n/a | n/a | n/a |
| noDR | 4 | 74. ± 6.0 | 1/3 | 0/4 | 13.5 ± 15.6 | 0/4 |
| PDR | 13 | 49.9 ± 9.3* | 3/10 | 8/5 | 21.6 ± 8.4 | 8/5 |

Diabetic Macular Edema (DME)
*P < 0.001

Proteomic analysis was performed on 50 µL of undiluted vitreous from non-diabetic mellitus (NDM) subject (n=5), patients with diabetes mellitus with no diabetic retinopathy (no DR, n=4), and patients with diabetic patients with PDR (n=3). Experienced ophthalmologists diagnosed diabetic retinopathy. Sample were separated by 12% SDS-PAGE, gels were stained with Coomassie™ brilliant blue stain, and the entire lane for each sample was divided equally into 60-70 slices of about 1 mm in width. Gel slices were individually digested with trypsin (Promega, Madison, Wis.) and analyzed by capillary liquid chromatography, nanospray ionization, and tandem mass spectroscopy using LTQ 2-dimensional linear ion trap mass spectrometer (Thermo Electron Corporation). Data acquisition parameters were full scan MS (range 400 to 1200 m/z) followed by 10 data-dependent MS/MS events.

Assignment of MS/MS data was performed using human subset of non-redundant protein database from National Center for Biotechnology Information and TurboSEQUES® (BioWorks™ 3.1, Thermo Electron Corporation). Resultant matches were entered and compiled into the MYSQL relational database and proteomics computational analyses were performed using the Hypertext Preprocessor-based interface according to the following algorithm: Peptide identifications were made based on the following criteria: Cross-correlation score >1.5, 2.0 and 2.5 for charge states +1, +2 and +3, respectively; Delta Correlation >0.1; Primary Score >200; Ranking of the Primary Score <3; and percent fragment ions >30%. Protein identifications were assigned when the following criteria were met: unique peptide match number ≥2, peptides contributing to protein matches were derived from a single gel slice or adjacent slices, and the protein was identified in at least 2 vitreous samples. The lower limit of detection was approximately 0.5 to 1 nM.

Protein matches for the 12 vitreous samples were compiled, and the numbers of unique peptides (median and mean ±SD) for each protein from the 3 groups of subject are shown in FIG. 4. The total number of proteins identified in the vitreous was 117, including 64, 113, and 107 proteins in the NDM, noDR, and PDR samples, respectively.

A semi-quantitative comparison of proteins identified in the three groups of vitreous samples (NDM, noDR, and PDR) was performed using the numbers of unique peptides identified by tandem mass spectroscopy for each protein and sample. Kruskal-Wallis analysis of ranks was used to identify differences ($P<0.05$) in protein appearance among the three groups. The correlations of carbonic anhydrase (-1 and -2) appearance with the presence of other proteins identified in the vitreous were determined using Spearman correlation coefficients.

Kruskal-Wallis analysis of ranks indicated that 31 proteins were differentially detected among the 3 groups ($P<0.05$) (Table 2), including transport proteins (afamin, apolipoprotein A-I, apolipoprotein A-IV, apolipoprotein B-100, apolipoprotein C-III, apolipoprotein D); acute-phase response proteins (alpha-1-antitrypsin, α-2-HS-glycoprotein, angiotensinogen (AGT), chitinase 3-like 1, orosomucoid-1 and -2); proteins involved in cell growth, maintenance, and metabolism-(carbonic anhydrase 1 (CA-1), GAPDH, gelsolin isoform a, pigmented epithelium-derived factor (PEDF)); complement activation (complement C4B, complement component 9, clusterin isoform 1); and cell adhesion proteins (α-2-glycoprotein 1-zinc, galectin-3 binding protein) (Ashburner et al., Nat. Genet. 25, 25-29 (2000)). Compared with NDM, there were 27, 18, and 31 proteins elevated in PDR, noDR and PDR+noDR groups, respectively. Conversely, amyloid proteins and Dickkopf related protein -3 were detected more frequently in NDM compared with PDR vitreous.

TABLE 2

Vitreous Proteins Differentially Detected in NDM, noDR, and PDR Subjects.

| Protein Name | gi number | NDM (n = 5) Median | NDM (n = 5) Mean ± SD | noDR (n = 4) Median | noDR (n = 4) Mean ± SD | PDR (n = 3) Median | PDR (n = 3) Mean ± SD | Group Differences Chi-square value | p |
|---|---|---|---|---|---|---|---|---|---|
| Actin, beta[1] | 14250401 | 0.0 | 0.4 ± 0.9 | 5.0 | 5.0 ± 2.9 | 6.0 | 6.0 ± 1.0 | 7.98[a,c] | 0.02 |
| Afamin[1,2] | 4501987 | 0.0 | 0.4 ± 0.9 | 2.5 | 2.8 ± 2.5 | 3.0 | 4.0 ± 1.7 | 6.48[c] | 0.04 |
| Alpha-1-antitrypsin[1,2] | 1703025 | 10.0 | 10.2 ± 1.5 | 23.0 | 22.5 ± 9.0 | 18.0 | 23.0 ± 10.4 | 6.81[a,c] | 0.03 |
| Alpha-2-glycoprotein 1-zinc[1,2] | 4502337 | 2.0 | 1.2 ± 1.1 | 4.0 | 5.8 ± 4.2 | 7.0 | 8.3 ± 2.3 | 8.69[a,c] | 0.01 |
| Alpha-2-HS-glycoprotein | 4502005 | 0.0 | 0.0 ± 0.0 | 3.0 | 3.0 ± 0.0 | 0.0 | 1.0 ± 1.7 | 8.49[a] | 0.01 |
| Angiotensinogen[1,2] | 15079348 | 2.0 | 1.2 ± 1.1 | 4.0 | 4.5 ± 2.5 | 7.0 | 6.7 ± 1.5 | 7.88[a,c] | 0.02 |
| Apolipoprotein A-I[1,2] | 4557321 | 8.0 | 7.6 ± 2.3 | 18.0 | 17.3 ± 6.8 | 14.0 | 19.0 ± 8.7 | 7.92[a,c] | 0.02 |
| Apolipoprotein A-IV[1,2] | 4502151 | 5.0 | 4.8 ± 1.3 | 15.0 | 18.0 ± 12.8 | 8.0 | 13.3 ± 9.2 | 7.32[a,c] | 0.03 |
| Apolipoprotein B-100[1,2] | 178730 | 0.0 | 0.0 ± 0.0 | 0.0 | 3.0 ± 6.0 | 3.0 | 2.7 ± 0.6 | 6.22[c] | 0.05 |
| Apolipoprotein C-III[1,2] | 4557323 | 0.0 | 0.0 ± 0.0 | 0.0 | 0.5 ± 1.0 | 2.0 | 2.0 ± 0.0 | 7.91[c] | 0.02 |
| Apolipoprotein D | 1246096 | 0.0 | 0.0 ± 0.0 | 2.0 | 2.3 ± 0.5 | 0.0 | 0.7 ± 1.2 | 8.51[a] | 0.01 |
| Beta globin[1,2] | 4504349 | 0.0 | 0.0 ± 0.0 | 3.0 | 4.5 ± 5.7 | 12.0 | 11.7 ± 1.5 | 7.62[c] | 0.02 |
| Carbonic anhydrase 1[2] | 4502517 | 0.0 | 0.0 ± 0.0 | 0.0 | 3.0 ± 6.0 | 12.0 | 11.0 ± 3.6 | 7.55[c] | 0.02 |
| Chitinase 3-like 1[1,2] | 14919433 | 0.0 | 0.8 ± 1.1 | 7.0 | 6.8 ± 4.4 | 10.0 | 10.7 ± 1.2 | 8.05[a,c] | 0.02 |
| Clusterin isoform 1[2] | 42716297 | 6.0 | 6.4 ± 2.5 | 13.0 | 13.0 ± 2.9 | 11.0 | 12.3 ± 4.2 | 7.39[a,c] | 0.03 |
| Complement C4B | 1314244 | 5.0 | 8.4 ± 4.8 | 22.0 | 22.0 ± 9.0 | 16.0 | 21.3 ± 10.1 | 6.08[a,c] | 0.05 |
| Complement component 9[1,2] | 4502511 | 0.0 | 0.0 ± 0.0 | 0.0 | 1.3 ± 2.5 | 5.0 | 4.3 ± 1.2 | 7.18[c] | 0.03 |
| Delta-globin[1,2] | 18462105 | 0.0 | 0.0 ± 0.0 | 0.0 | 2.0 ± 4.0 | 6.0 | 6.3 ± 1.5 | 6.63[c] | 0.04 |
| Galectin-3 binding protein | 5031863 | 0.0 | 0.0 ± 0.0 | 2.5 | 2.0 ± 1.4 | 0.0 | 0.0 ± 0.0 | 7.20[a] | 0.03 |
| GAPDH[1] | 31645 | 0.0 | 0.4 ± 0.9 | 0.0 | 0.5 ± 1.0 | 4.0 | 4.0 ± 2.0 | 6.77[b,c] | 0.03 |
| Gelsolin isoform a | 4504165 | 5.0 | 4.2 ± 1.1 | 9.5 | 9.8 ± 3.3 | 10.0 | 11.0 ± 4.6 | 8.35[a,c] | 0.02 |
| Hemoglobin alpha-1 globin chain[1,2] | 13650074 | 0.0 | 0.0 ± 0.0 | 2.5 | 3.5 ± 4.4 | 9.0 | 9.0 ± 1.0 | 7.62[c] | 0.02 |
| Lucine-rich alpha-2-glycoprotein 1[1,2] | 16418467 | 0.0 | 0.0 ± 0.0 | 1.5 | 1.5 ± 1.7 | 3.0 | 4.0 ± 1.7 | 7.56[c] | 0.02 |
| Myosin VA | 10835119 | 5.0 | 4.6 ± 2.7 | 0.0 | 0.0 ± 0.0 | 3.0 | 2.3 ± 2.1 | 6.17[a] | 0.05 |
| Neuropolypeptide h3[1,2] | 4261934 | 0.0 | 0.0 ± 0.0 | 0.0 | 0.0 ± 0.0 | 2.0 | 1.7 ± 1.5 | 6.55[c] | 0.04 |
| Orosomucoid 1[1,2] | 20070760 | 4.0 | 4.4 ± 0.9 | 7.0 | 6.8 ± 1.5 | 8.0 | 8.7 ± 1.2 | 8.33[a,c] | 0.02 |
| Orosomucoid 2[1,2] | 4505529 | 3.0 | 3.2 ± 0.8 | 5.5 | 5.8 ± 2.1 | 9.0 | 8.0 ± 1.7 | 7.72[a,c] | 0.02 |
| PEDF | 1144299 | 10.0 | 9.2 ± 1.6 | 12.0 | 12.0 ± 1.8 | 13.0 | 13.3 ± 0.6 | 6.74[c] | 0.03 |

TABLE 2-continued

Vitreous Proteins Differentially Detected in NDM, noDR, and PDR Subjects.

| Protein Name | gi number | NDM (n = 5) | | noDR (n = 4) | | PDR (n = 3) | | Group Differences | |
|---|---|---|---|---|---|---|---|---|---|
| | | Median | Mean ± SD | Median | Mean ± SD | Median | Mean ± SD | Chi-square value | p |
| Plasma retinol-binding protein[1,2] | 20141667 | 0.0 | 0.0 ± 0.0 | 3.0 | 2.8 ± 2.2 | 4.0 | 4.0 ± 1.0 | 7.30[a,c] | 0.03 |
| Transferrin[2] | 37747855 | 15.0 | 15.2 ± 1.1 | 24.5 | 24.3 ± 3.9 | 21.0 | 23.3 ± 8.7 | 7.39[a,c] | 0.03 |
| Transthyretin[1,2] | 30584579 | 5.0 | 4.8 ± 0.8 | 7.0 | 7.3 ± 2.6 | 10.0 | 9.0 ± 1.7 | 6.13[c] | 0.05 |

The range, median, mean and standard deviation for the number of unique peptides for proteins in each group are shown.
Superscripts "a," "b," and "c" indicate differences between NDM vs DM noDR, DM noDR vs PDR, and NDM vs PDR, respectively, ($P < 0.05$). Changes in protein appearance that correlated ($P < 0.05$) with changes in carbonic anhydrase-1 and -2 levels are indicated with the superscripts "1" and "2", respectively.

Western blot analysis was used to further quantify changes in the expression of some of these proteins among the 3 study groups. Vitreous was separated by SDS-PAGE and immunoblotted using primary antibodies against C1-Esterase inhibitor (CalBioChem, Inc, San Diego, Calif.); angiotensinogen (Santa Cruz Biotechnology, Santa Cruz, Calif.); pigment-epithelium derived factor (PEDF, CHEMICON International, Inc, Temecula, Calif.); and Carbonic anhydrase I and carbonic anhydrase II (Abcam, Inc., Cambridge, Mass.). Results were visualized by enhanced chemiluminescence (Cell Signaling, Beverly, Mass.).

Figure 1A:
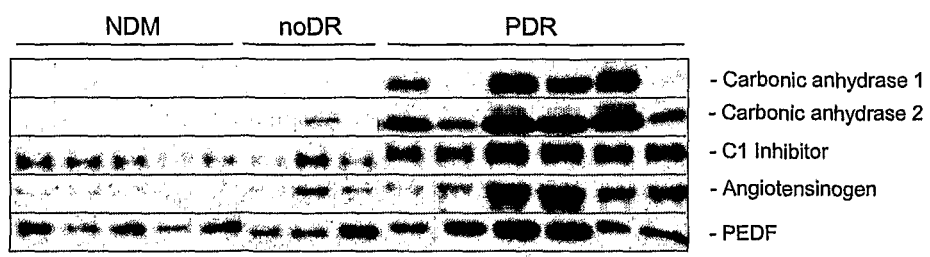
FIG. 1A is a composite of four Western blots showing immunoreactivity of carbonic anhydrase 1, carbonic anhydrase 2, C1 inhibitor, angiotensinogen and Pigment Epithelium-Derived Factor (PEDF) proteins in vitreous samples from non-diabetic mellitus (NDM) subjects, patients with diabetes mellitus and no diabetic retinopathy (noDR), and diabetic patients with PDR+/−DME (PDR). (Bottom panel).
Figure 1B:
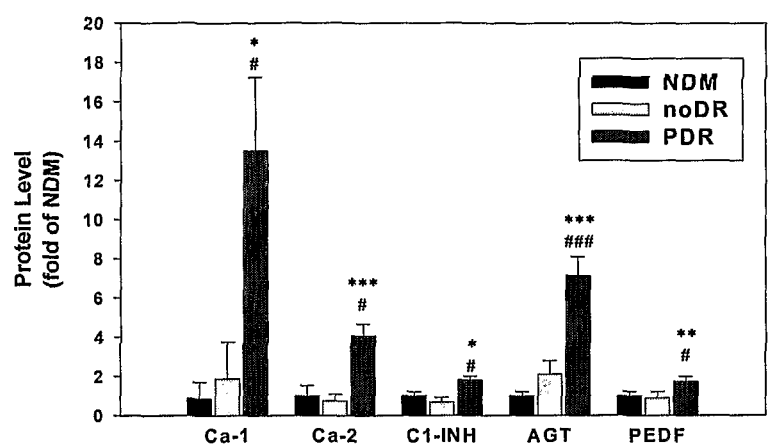
FIG. 1B is a bar graph quantifying the western blot results for each protein among the 3 groups of samples (NDM, n=9; noDR n=4, PDR, n=7). Comparisons vs NDM indicated as *P<0.05, <0.01, *<0.005. Comparisons vs noDR are shown as #P<0.05, ###<0.005.

Two carbonic anhydrase isoforms were detected in vitreous. PDR was associated with 13.5 (P<0.05) and 7.2 (P<0.05) fold increases in carbonic anhydrase 1 (CA-1) levels in vitreous compared with NDM and noDR groups, respectively (FIG. 1). Comparison with purified CA-1 standards demonstrated that the concentration of CA-1 in the vitreous ranged from 1 to 10 ng/ul in vitreous from the PDR group. Vitreous from PDR subject also contained an increased concentration of carbonic anhydrase 2 (CA-2), which was elevated by 4 fold (P<0.001) and 5.6 fold (P<0.05) compared with the noDR and NDM groups, respectively. In addition, PDR subjects had increased levels of C1-INH (1.8 fold, P<0.05), AGT (7.1 fold, P<0.001), and PEDF (1.4 fold, P<0.01) compared with vitreous from the NDM group (FIG. 1).

Example 2

Effect of Carbonic Anhydrase 1 (CA-1) on Retinal Vascular Permeability (RVP)

The effects of intravitreal injections of proteins shown in FIG. 1 on RVP in rats were examined.

To measure retinal vascular permeability, 265 male Sprague Dawley and 12 male Long-Evans rats (Taconic Farms, Germantown, N.Y.) with initial body weights of 250 g were used. Experiments were performed in accordance with guidelines from the Association for Research in Vision and Opthalmology and approval from the Animal Care and Use committee of the Joslin Diabetes Center. Video fluorescein angiography was performed using a scanning laser opthalmoscope (Rodenstock Instrument, Munich, Germany) (Horio et al., Diabetologia 47:113-123 (2004)). Vitreous fluorophotometry and administration of fluorescein-dextran was performed as described previously (Aiello et al., Diabetes 46:1473-1480 (1997)).

Figure 2A:
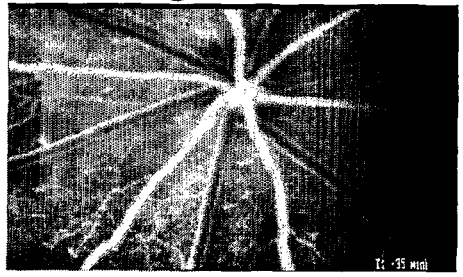
FIGS. 2A-F are fluorescein angiogram of rat retina at baseline (2A) and 30 minutes after intravitreal injection of balanced saline solution (BSS) (2C, a vehicle control) and CA-1 (2B), and co-injection with CA-1 and acetazolamide (2D), and 48 hours after intravitreal injection with BSS (2E) and CA-1 (2F). Focal areas of fluorescein accumulation and leakage are indicated with an arrow and a bracket, respectively, in 2F.
Figure 2B:
Figure 2C:
Figure 2D:
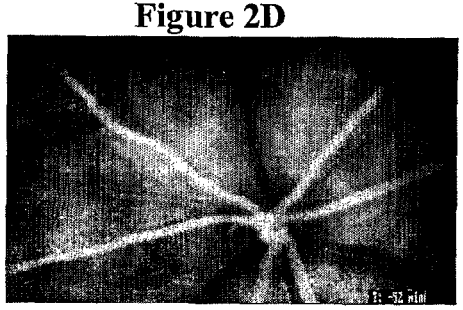
Figure 2E:
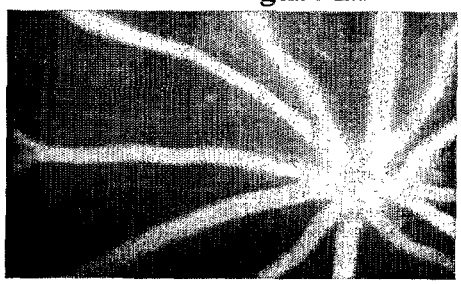
Figure 2F:
Figure 2G:
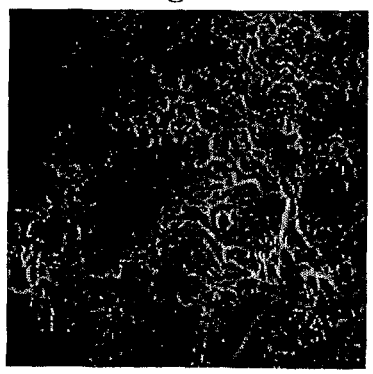
FIGS. 2G-H are confocal (10×) fluorescence micrographs of retinal flatmounts, 48 hours after intravitreal injection of BSS (2G) and CA-1 (2H). Focal areas of fluorescein accumulation and leakage are indicated with arrows.
Figure 2H:
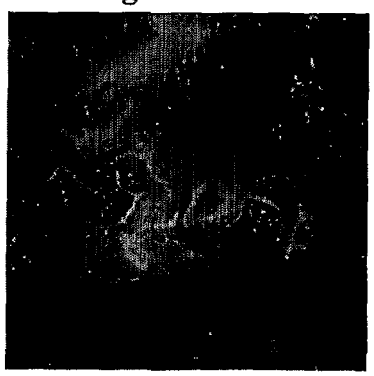

Carbonic anhydrase was not detected by either mass spectroscopy or western blot analysis in the vitreous of untreated Sprague Dawley rats. Injection of CA-1 into the rat vitreous, at a concentration that was observed in the vitreous of patients with PDR (2 µg/ml), induced increased retinal fluorescein leakage at 30 minutes as compared to baseline or eyes that received a control intravitreal injection of balanced saline solution (BSS, FIGS. 2A and 2C vs 2B). The increase in RVP induced by CA-1 was blocked by co-injection with the carbonic anhydrase inhibitor acetazolamide (10 µM) (FIGS. 2C vs 2D), indicating that the CA-1 enzymatic activity was necessary for its effect on RVP. At 48 hours after intravitreal CA-1 injection, focal areas of retinal vascular leakage were observed using both fluorescein (FIG. 2e vs 2f) and 2000 kDa fluorescein-dextran conjugate (FIG. 2g vs 2h).

Intravitreal injection of CA-1 increased RVP, as measured by vitreous fluorophotometry, in a dose-dependent manner (FIG. 3A), with a maximal increase of 2.3 fold (p<0.05) at 2 µg. The $EC_{50}$ of CA-1 was 67 ng, which corresponds to a final concentration of about 670 pg/µL following dilution in 100 uL of rat vitreous. CA-1 induced RVP was inhibited 68% by co-injection of 10 µM acetazolamide (p<0.05) which had no effect on basal RVP. Intravitreal injection of 200 ng carbonic anhydrase-2 (CA-2) induced an increase in RVP to an extent similar to that observed with CA-1. The effect of a single dose of CA-1 on RVP was sustained at 59% over control at 24 hours post injection (FIG. 3B).

Intravitreal CA-1 at 200 ng/eye (20 µg/ml) increased RVP by 2.4-fold (P<0.05) from 7.4 au in control BSS injected eyes to 17.4 au (FIG. 3e). The RVP induced by CA-1 was comparable in magnitude to 14.5 au in eyes receiving an intravitreal injection of VEGF and the two responses were additive (26 au, P<0.05 vs VEGF alone) (FIG. 3C).

Figure 4C:
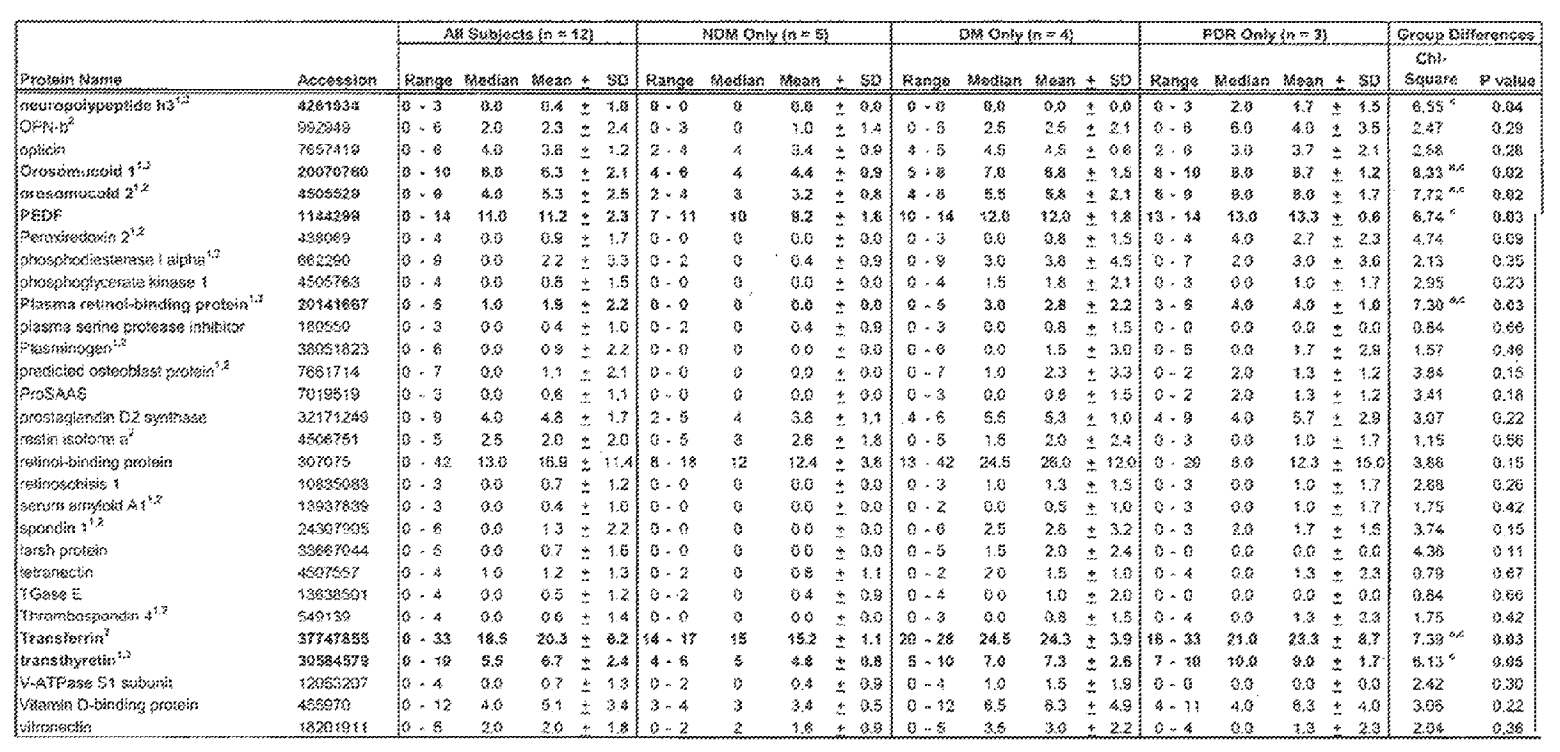

Co-injection of C1-INH reduced CA-1 stimulated RVP by 92% (P<0.05) whereas C1-INH did not affect VEGF-induced retinal fluorescein permeability. Co-injection of other serpin family proteins, including angiotensinogen (and PEDF, not shown), did not block CA-1 induced permeability (FIG. 4C). These results show that CA-1 induced RVP is mediated by a C1-INH sensitive pathway and independent of VEGF's effect on permeability.

Although the role of C1-INH in angioedema is well documented (Pappalardo et al., J. Allergy Clin. Immunol. 114: 638-644 (2004); Zahedi et al., J. Clin. Invest. 95:1299-1305 (1995); Carugati et al., Mol. Immunol. 38:161-173 (2001)), its role in retinal edema has not yet been described. C1-INH deficiency has been shown to increase vascular permeability via increased bradykinin generation and the BK2 receptor pathway (Han et al., J. Clin. Invest. 109:1057-1063 (2002)). Co-injection of the BK2- or BK1 receptor antagonists Hoe 140 and desHoe 140 with CA-1 decreased RVP by 67% and 45%, respectively (FIG. 3D). The combined treatment with both antagonists reduced CA-1 induced permeability by 78%. Previous studies have shown that carboxypeptidase inhibitors leupeptin or aprotinin block proteolytic activation of kallikrein (Shariat-Madar et al., J. Biol. Chem. 277:17962-

17969 (2002); Shariat-Madar et al., Blood 103:4554-4561 (2004)). Intravitreal injection of 100 μM leupeptin or aprotinin reduced CA-1 stimulated RVP by 71% and 50%, respectively (FIG. 3E). These protease inhibitors did not affect fluorescein permeability in control BSS-injected eyes. Since bradykinin can induce permeability via activation of nitric oxide synthase (NOS), the effect of NOS inhibition on CA-1 induced permeability was investigated. Intravitreal injection with Nitro-L-arginine methyl ester (100 μM) inhibited CA-1 induced RVP by 62% ($P<0.05$).

These data demonstrate that the presence of elevated CA-1 in the eye is sufficient and necessary to cause increased vascular permeability.

Example 3

Effect of Injection of Human Vitreous on Retinal Vascular Permeability (RVP)

To evaluate the contribution of carbonic anhydrase activity in human vitreous to RVP, vitreous from the human subjects was transplanted into the rat in the absence or presence of pretreatment with 10 μM acetazolamide. In these tests, 10 μl of human vitreous was injected into the rat vitreous compartment and the response on retinal vascular permeability was measured. The human vitreous was pretreated for 10 mins with acetazolamide or BSS vehicle.

Vitreous fluorescein leakage was higher in rat eyes injected with 10 μL of vitreous from patients with PDR compared with vitreous from subjects without PDR ($P=0.02$) and BSS control ($P<0.05$). Acetazolamide reduced RVP in rat eyes injected with vitreous from subjects with PDR from 13.67±5.23 to 9.20±3.85 ($P=0.017$, $n=5$). Acetazolamide did not affect RVP in rat eyes injected with vitreous obtained from subjects in the noDR ($n=3$) and NDM groups ($n=4$) (FIG. 3F).

These data demonstrate that human vitreous from patients with PDR increases RVP when injected intravitreally in the rat eye.

Example 4

Carbonic Anhydrase in the Vitreous Induces Clinically Relevant Intraretinal Edema Although increased RVP can occur within 1 week of diabetes onset (Miyamoto et al., Proc Natl. Acad Sci U.S.A. 96:10836-10841 (1999)), early diabetes alone is usually not sufficient to induce intraretinal thickening because the eye has numerous mechanisms to equilibrate fluid balance. Furthermore, animal models of diabetes generally do not result in actual retinal edema, even though increased RVP is evident. It was postulated that the combined effect of diabetes and intravitreous CA-1 on the retina might exceed the counter-regulatory mechanisms involved in ocular fluid balance and lead to retinal thickening. Since focal areas of leakage to fluorescein-dextran were found at 48 hours post-intravitreal injection (FIG. 2), this time point was used to further investigate the effect of intravitreal injection of CA-1 on retinal ultrastructure using high-speed, ultrahigh resolution optical coherence tomography (OCT) (Wojtkowski et al., Opthalmology, 112(10):1734-46 (2005)).

Rats had diabetes induced by intraperitoneal injection of streptozotocin (55 mg/kg) after overnight fast. Diabetes was confirmed after 24 hours with blood glucose greater than 250 mg/dl. After 2 weeks of diabetes, rats were injected intravitreally with CA-1 or BSS and the retinas imaged by OCT after 48 hours. Retinal ultrastructure was imaged and quantitatively measured using a high-speed, ultrahigh resolution OCT system with Fourier/spectral domain detection. Using a broadband superluminescent diode light source (Superlum Diodes Limited, Moscow, Russia) with a 155 nm bandwidth, a 2.6 μm axial resolution in tissue was achieved after digital spectral shaping. The imaging speed was 26,000 axial scans per second and the system sensitivity was 96 dB with an axial (depth) scan range of 1.3 mm in tissue. The OCT research instrument was designed for small animal retinal imaging and used a post-objective scanning microscope with a 10 μm transverse resolution. Corneal refraction was compensated with a coverslip and Goniosol (CIBA Vision Ophthalmics). Each data set consisted of 256 images with 512 axial scans per image, acquired in a raster pattern on the retina. Measurements of intraretinal layer thicknesses were performed on individual cross sectional OCT images.

Using OCT imaging with 2.6 mm axial image resolution to visualize and measure retinal morphology, we observed that at 48 hours after intravitreal injection, the retina in diabetic rat eyes receiving CA-1 was 12% thicker and the outer nuclear layer (ONL) was 30% thicker than the contralateral eye that had received an intravitreal saline vehicle injection. Indeed, in CA-1 treated eyes the ONL accounted for 38% of the overall retinal thickness, a 17% and 18% increase compared with BSS-treated diabetic rats and nondiabetic rats, respectively. These data provide the first evidence of an endogenous molecule that induces clinically evident intraretinal edema in the diabetic rat model at physiologically relevant concentrations.

Example 5

Extracellular Carbonic Anhydrase Increases Blood-Brain Barrier Permeability

The appearance of CA-1 in the vitreous correlated with the presence of 14 other proteins ($P<0.001$), including plasma proteins (α2-plasmin inhibitor, apolipoproteins A-II, B-100, and C-III, complement C9 and factor H, fibrinogen γ chain, kininogen, and leucine-rich α2-glycoprotein 1) (Anderson et al., Mol Cell Proteomics. 3, 311-326 (2004)) and cytoplasmic erthrocyte proteins, including bilverdin reductase B and hemoglobin alpha, beta, and delta chains (Table 2). Since both CA-1 and CA-2 are cytoplasmic proteins expressed in erythrocytes and ocular tissues (Wistrand et al., Invest. Opthalmol. Vis. Sci. 27, 419-428 (1986)), the increased appearance of these isoforms in the PDR vitreous could be the result of local tissue injury or lysed red blood cells (RBC) from intraocular hemorrhage. Given the prevalence of retinal and vitreous hemorrhage in PDR, and the high abundance of CA-1 in RBC, the appearance of CA-1 in the vitreous could be derived from lysed RBC. However, it is unlikely that the blood is a result of the vitrectomy surgery, as elevated levels of CA were not identified in patients without PDR who underwent vitrectomy.

To test our hypothesis that carbonic anhydrase derived from lysed RBC could induce RVP we injected lysed RBC into the vitreous of rats.

To prepare lysed RBCs, 3 ml rat blood in 15 ml saline was centrifuged at 1,000 g for 10 minutes; the plasma and buffy coat were discarded. The RBCs were then washed in 12 ml saline. The packed cells were frozen in liquid nitrogen for 5 minutes and then allowed to thaw at room temperature. The lysed RBCs were centrifuged at 12,000 rpm for 30 minutes. The supernatant was used for experiment. The vitreous of rat eyes were injected with BSS, CA-1, lysed RBCs, or lysed RBCs plus acetazolamide in 10 μl final volume. Approximate 21 hours later, Evans blue was injected at a dosage of 30 mg/kg. After the dye had circulated for 3 hours the rats were perfused via the left ventricle with saline. The retina were harvested and Evans blue dye was extracted by incubation in 0.3 ml formamide for 20 hours at 60° C. The extract was centrifuged (14,000 rpm for 30 minutes). The absorbance of the filtrate was measured with a spectrophotometer at 620 nm. The concentration of dye in the extracts was calculated from a standard curve.

Intravitreal injection of lysed RBC or CA-1 into rats increased RVP to 4.1 fold and 3.0 fold, respectively, compared with eyes that received a BSS injection (FIG. 3d). Pretreatment of lysed RBC with acetazolamide (10 µM) blocked the increase in RVP by lysed RBC (P<0.05). These results suggest that the release of CA-1 into the vitreous from an intraocular hemorrhage could increase RVP.

To determine whether extracellular carbonic anhydrase could have broad relevance to vasogenic edema, the effect of CA-1 on blood brain barrier permeability was investigated. Previous reports have shown that factor(s) released from lysed RBCs induce edema following intracerebral hemorrhage (Xi et al., Stroke 32:2932-2938 (2001)). Indeed, factors released from the hematoma to the brain parenchyma have been implicated in the delayed onset of cerebral edema and secondary neuronal injury in the days following an intracerebral hemorrhage (Qureshi et al., N. Engl. J. Med. 344:1450-1460 (2001)).

To evaluate blood-brain barrier integrity, CA-1, BSA, C1-INH, lysed RBCs or BSS control were perfused into the subdural space 1 mm inferior to the bregma and 1 mm ventral to the skull surface. Approximately 22 hours later, 0.7 ml Evans blue was injected through a jugular vein catheter. After the dye circulated for 120 minutes, the rats were perfused with 50 ml saline through the left ventricle at 110 mmHg pressure. After decapitation, the brain was weighed and Evan's blue was extracted by incubating each brain in 1 ml of formamide for 20 hours at 60° C. The extract was centrifuged (14,000 rpm for 30 minutes). The absorbance of the filtrate was measured with a spectrophotometer at 620 nm. The concentration of dye in the extracts was calculated from a standard curve of Evans blue in formamide, normalized to the brain weight, and expressed per gram of tissue.

In this rat model, infusion of CA-1 or lysed RBC into the subdural space 1 mm inferior to the bregma and 1 mm ventral to the skull surface induced intense focal areas of Evan's blue leakage on the posterior and anterior surfaces of the brain (FIGS. 5d-5i), which were not observed in rats that received an infusion with BSS vehicle (FIGS. 5a-c). CA-1 induced cerebral vascular permeability occurred in areas distal to the infusion site, consistent with the diffusion of CA-1 in the cerebral fluid. Quantification of Evan's blue dye showed that CA-1 and lysed RBC increased permeability in brain by 2.3 fold and 2.2 fold respectively compared to rats that received BSS (P<0.05, FIG. 5j). In contrast, rats that received C1-INH or albumin had similar or slightly lower levels of permeability compared with BSS control. Similar to our findings for RVP (FIG. 3e), C1-INH blocked CA-1-induce cerebral vascular permeability.

These results suggest that the release of CA-1 from lysed RBCs following cerebral hemorrhage contributes to increased blood-brain barrier permeability and edema.

Additional References

Yamane et al., Mol. Cell. Proteomics. 2:1177-1187 (2003)
Sun et al., Am. J. Physiol. Cell Physiol. 284:C1114-C1122 (2003)
Sun et al., Exp. Eye. Res. 77:287-295 (2003)
Sun et al., BMC Physiol. 4:8 (2004)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing retinal vascular permeability in the eye of a human subject, the subject having increased retinal vascular permeability or edema in the eye, the method comprising administering to the subject a therapeutically effective amount of DX-88 (SEQ ID NO: 1).

2. The method of claim 1, wherein the administering is local administration to the eye of the subject.

3. The method of claim 2, wherein the local administration is by injection into the vitreous or aqueous humor of the eye.

4. The method of claim 1, wherein said subject has diabetic macular edema, proliferative diabetic retinopathy, or nonproliferative diabetic retinopathy.

5. The method of claim 1, wherein said subject has macular degeneration.

6. The method of claim 1, wherein said subject has a retinal vein occlusion.

7. A method of decreasing retinal vascular permeability in the eye of a subject, the subject having increased retinal vascular permeability or edema in the eye, the method comprising administering to the subject a therapeutically effective amount of complement-1 inhibitor polypeptide.

8. The method of claim 7, wherein the administering is local administration to the eye of the subject.

9. The method of claim 8, wherein the local administration is by injection into the vitreous or aqueous humor of the eye.

10. The method of claim 7, wherein said subject has diabetic macular edema, proliferative diabetic retinopathy, or nonproliferative diabetic retinopathy.

11. The method of claim 7, wherein said subject has macular degeneration.

12. The method of claim 7, wherein said subject has a retinal vein occlusion.

13. The method of claim 7, wherein said subject s a human.

14. A method of decreasing retinal vascular permeability in the eye of a human subject, the subject having increased retinal vascular permeability or edema in the eye, the method comprising administering to the subject a therapeutically effective amount of an anti-prekallikrein antibody or an antigen-binding fragment thereof, wherein the antibody or antigen-binding fragment recognizes human prekallikrein.

15. The method of dam 14, wherein the administering is local administration to the eye of the subject.

16. The method of claim 15, wherein the local administration is by injection into the vitreous or aqueous humor of the eye.

17. The method of claim 14, wherein said subject has diabetic macular edema, proliferative diabetic retinopathy, or nonproliferative diabetic retinopathy.

18. The method of claim 14, wherein said subject has macular degeneration.

19. The method of claim 14, wherein said subject has a retinal vein occlusion.

* * * * *